(12) United States Patent
Li et al.

(10) Patent No.: US 11,753,650 B2
(45) Date of Patent: Sep. 12, 2023

(54) WHEAT FERTILITY-RELATED GENE TAMS7 AND APPLICATION METHOD THEREOF

(71) Applicants: FRONTIER LABORATORIES OF SYSTEMS CROP DESIGN CO., LTD., Beijing (CN); PEKING UNIVERSITY INSTITUTE OF ADVANCED AGRICULTURAL SCIENCES, Shandong (CN)

(72) Inventors: Jian Li, Beijing (CN); Zheng Wang, Beijing (CN); Ligeng Ma, Beijing (CN); Xingwang Deng, Beijing (CN)

(73) Assignees: BEIJING NEXT GENERATION HYBRID WHEAT BIOTECHNOLOGY CO., LTD, Beijing (CN); PEKING UNIVERSITY INSTITUTE OF ADVANCED AGRICULTURAL SCIENCES, Shandong (CN)

( * ) Notice: Subject to any disclaimer, the term of this patent is extended or adjusted under 35 U.S.C. 154(b) by 192 days.

(21) Appl. No.: 16/611,863

(22) PCT Filed: Nov. 8, 2017

(86) PCT No.: PCT/CN2017/109813
§ 371 (c)(1),
(2) Date: Nov. 8, 2019

(87) PCT Pub. No.: WO2018/205521
PCT Pub. Date: Nov. 15, 2018

(65) Prior Publication Data
US 2021/0139931 A1 May 13, 2021

(30) Foreign Application Priority Data
May 9, 2017 (CN) .......................... 201710321452.3

(51) Int. Cl.
*C12N 15/82* (2006.01)
(52) U.S. Cl.
CPC ..... *C12N 15/8289* (2013.01); *C12N 15/8213* (2013.01); *C12N 15/8231* (2013.01)

(58) Field of Classification Search
None
See application file for complete search history.

(56) References Cited

U.S. PATENT DOCUMENTS

2015/0353958 A1* 12/2015 Tang .................. C12N 15/8289
800/278
2016/0255782 A1 9/2016 Zhou et al.

FOREIGN PATENT DOCUMENTS

EP 2918681 A1 9/2015
WO 2018022410 A1 2/2018

OTHER PUBLICATIONS

NCBI Reference Sequence: XM_020320296.1. "Predicted: *Aegilops tauschii* subsp. *tauschii* protein Hothead-like (LOC109761481), mRNA" GenBank, Feb. 24, 2017.
GenBank: AK376315.1. "*Hordeum vulgare* subsp. *vulgare* mRNA for predicted protein, complete cds, clone: NIASHv3120L16" GenBank, May 20, 2011.
Extend European Search Report cited in 18940891.7 dated Jan. 22, 2022, 7 pages.

* cited by examiner

*Primary Examiner* — Weihua Fan
*Assistant Examiner* — Brian James Sullivan
(74) *Attorney, Agent, or Firm* — Gang Yu

(57) ABSTRACT

The application discloses a wheat fertility-related gene TaMS7 and an application method thereof, and belongs to the field of biotechnology. By analyzing a genome-wide expression profile of wheat anthers at different development stages, we obtain the wheat fertility-related gene TaMS7, and regulate the fertility of a plant by adjusting expression of the gene to produce and maintain wheat male sterility lines and to prepare hybrid seeds, wherein the discovery of this gene has important theoretical and practical significance for establishing an efficient technology system of wheat hybrid seed production, and for studying wheat male sterility mechanism and heterosis.

17 Claims, 2 Drawing Sheets
Specification includes a Sequence Listing.

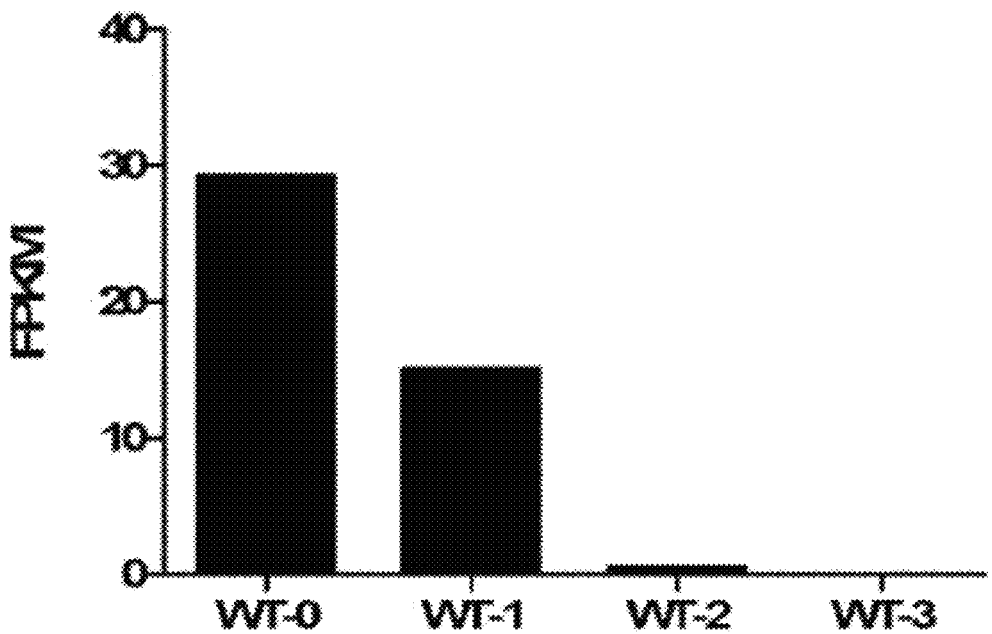
Fig. 1
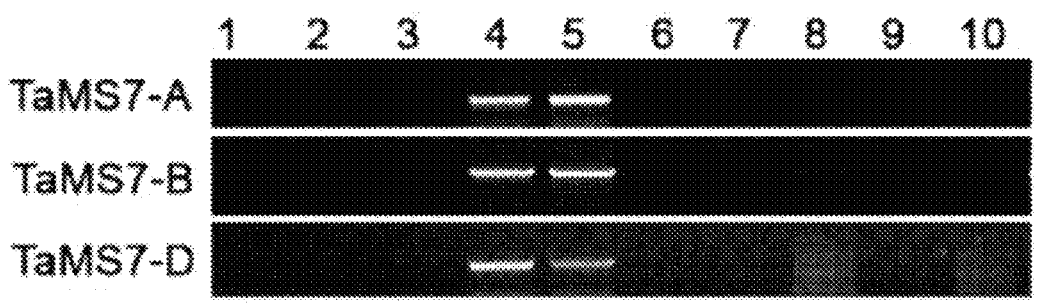
Fig. 2
Fig. 3

SEQUENCE LISTING

```
<160> NUMBER OF SEQ ID NOS: 36

<210> SEQ ID NO 1
<211> LENGTH: 1923
<212> TYPE: DNA
<213> ORGANISM: Triticum aestivum L.

<400> SEQUENCE: 1
atggcacttg gccgcgcgag atcgccggcg ctggtgctcg ccgccgccgt ccttggcgcg      60
ctctgcgtcg tcgcgctctc ggaggatggt gcgtgtgttc ggggttttgc atgtcagcta     120
gtacggagta cgtgcctgtg tctgttatca tgatcaatga ccgatggtgg cgtgcgtgtg     180
cagagcaact ggagaacctg cggttcgtgc agcacgcgca ggacgcgccg ctggtgtcgc     240
actacaacta catcgtggtg ggcggcggca cgtccgggtg cccgctggcg gcgacgctgt     300
cggagcactc gcgggtgctg ctgctggagc gcggggcct cccctaccgc aacatgtcca      360
accaggagca cttcacggac gcgctggccg acacgtcgct ggcgtccccg gcgcagcggt     420
tcgtgtccac ggacggcgtg gtgaacgcgc gggcgcgggt gctgggcggc gggagctgcc     480
tcaacgccgg gttctacacg cgggccagca acgagtacgt gcgcacggcc gggtgggacg     540
ccggcctcgt caactcgtcg taccggtggg tggagcgcgc gctggtgttc cgcccggacg     600
tgccgccgtg gcaggccgcg ctccgggacg cgctgctgga ggccggcgtc acccccgaca     660
acggcttcac cttcgaccac gtcacgggga ccaagatcgg cggcaccatc ttcgacaaca     720
acgggcagcg ccacacggcc gccgacttcc tccggcacgc ccgccgcgg gggctcaccg      780 tggtgctcta cgccacggtg tcgcgggtcc tgttcaggag ccaggagggg gtgccgtacc     840
cggtggcgta cggggtggtg ttcgcggacc cgctgggggt gcagcaccgg gtgtacctcc     900
gggacggggg caagaacgag gtgatcctgt cggcggggac gctggggagc ccgcagctgc     960
```

-continued

| | |
|---|---|
| tgatgctgag cggcgtgggc ccgcaggtgc acctggaggc gcacagcatc caggtgctgg | 1020 |
| tggaccagcc catggtcggg cagggcgtgg ccgacaaccc catgaactcg gtcttcatcc | 1080 |
| cgtcgccggt gccggtgggg ctgtccctgg tgcaggtcgt cgggatcacc aagtccggca | 1140 |
| gcttcatcga gggcgtgagc ggctccgagt tcggcatccc ggtgtccaac ggcgcccgcc | 1200 |
| ggctggccag cttcgggctc ttctccccgc agaccgggca gctcggcacg ctgccgccgg | 1260 |
| ggcagaggac gccggaggcg ctgcagcgcg cggcggaggc gatgcggcgg ctggacaggc | 1320 |
| gggcgttccg gggcggcttc atcctggaga agatcctggg gccggtgtcg acggggcaca | 1380 |
| tcgagctgcg cagcaccgac ccgcgcgcca acccggccgt gaccttcaac tacttccagg | 1440 |
| aggcggagga cctggagcgg tgcgtccggg ggatccagac gatcgagcgg gtgatccagt | 1500 |
| cgcgcgcctt ctccaacttc acctacgcca acaccaccgt ggagtccatc ttcaccgact | 1560 |
| cggccaactt ccccgtcaac ctgctgccgc gccacgtcaa cgactcccgc tcgccggagc | 1620 |
| agtactgcag ggagaccgtc atgaccatct ggcactacca cggcgggtgc cacgtcggcg | 1680 |
| ccgtcgtcga cgacaactac cgggtgttcg gggtcagggg gctcagggtc atcgacagct | 1740 |
| ccaccttcag gtactccccc ggcaccaacc cgcaggccac cgtcatgatg ctcggcaggt | 1800 |
| aaacgcaact ctcaaatcac ccccgcaatt atactgatct gaatgaactc aactaacaca | 1860 |
| actgttgtaa atctgtacag gtatatgggc ataaagattc aggccgagag atggaggaaa | 1920 |
| tga | 1923 |

<210> SEQ ID NO 2
<211> LENGTH: 1954
<212> TYPE: DNA
<213> ORGANISM: Triticum aestivum L.

<400> SEQUENCE: 2

| | |
|---|---|
| atggcacttg gccgcgcgag atcaccggcg ctggtgctcg ccgccgccgt tcttggcgcg | 60 |
| ctctgcatcg tcgcactctc ggaggatggt gcgtgtgttc acctgcatgg tttttctggg | 120 |
| ggttttgcgt cagctacgtg cgtgtgtctt ttatcatgat caatggacgc tgtgatgatc | 180 |
| aatggtgccg tgcgtgtgca gagcaactgg agaacctgcg gttcgtgcag cacgcgcagg | 240 |
| acgcgccgct ggtgtcgcac tacaactaca tcgtggtcgg cggcggcacg tccgggtgcc | 300 |
| cgctggcggc gacgctgtcg gagcactcgc gggtgctcct gctggagcgc ggggcctcc | 360 |
| cctaccgcaa catgtcgaac caggagcact tcacggacgc gctggccgac acgtcgctgg | 420 |
| cgtccccggc ccagcggttc atctccacgg acggcgtggt gaacgcgcgg gcgcgggtgc | 480 |
| tgggcggcgg gagctgcctc aacgccggat tctacacgcg ggccagcaac gagtacgtgc | 540 |
| gcacggccgg gtgggacgcc ggcctcgtga actcgtcgta cggtgggtg gagcgcgcgc | 600 |
| tggtgttccg ccccgacgtg ccgccgtggc aggccgcgct ccgggacgcg ctgctcgagg | 660 |
| ccggcgtcac ccccgacaac ggcttcacct tcgatcacgt cacggggacc aagatcggcg | 720 |
| gcaccatctt cgacaacaac gggcagcgcc acacggccgc cgacttcctc cggcacgccc | 780 |
| ggccccgggg gctcaccgtc gtgctctacg ccacggtgtc ccggatcctg ttcagaagcc | 840 |
| aggaggggggt gccgtatccg gtggcgtacg gggtggtgtt cgcggacccg ctggggggtgc | 900 |
| agcaccgggt gtacctccgg gacgggggga agaacgaggt gatactgtcg gcggggacgc | 960 |
| tggggagccc gcagctgctg atgctgagcg gcgtcggccc gcaggcgcac ctcgaggcac | 1020 |
| acggcatcca ggtgctggtg gaccagccca tggtcgggca gggcgtggcc gacaaccccca | 1080 |

-continued

| | |
|---|---|
| tgaactcggt cttcatcccg tcgccggtgc cggtggggct ctccctggtg caggtcgtcg | 1140 |
| ggatcaccaa gtccggcagc ttcatcgagg gcgtgagcgg ctccgagttc ggcatcccgg | 1200 |
| tctccgacgg cgcccgccgc ctggccagct tcggcctctt ctcccccag accgggcagc | 1260 |
| tcggcacgct gccgccgggg cagaggacgc cggaggcgct gcagcgcgcg gcggaggcga | 1320 |
| tgaggcggct ggacaggcgg gcgttccggg gcgggttcat cctggagaag atcctggggc | 1380 |
| cggtgtccac gggccacatc gagctgcgca gcaccgaccc gcgcgcgaac ccggcggtga | 1440 |
| cgttcaacta cttccaggag gcggaggacc tggagcggtg cgtccggggg atccagacga | 1500 |
| tcgagcgggt gatccagtcg cgcgccttct ccaacttcac ctacgccaac accaccgtcg | 1560 |
| agtccatctt caccgactcg gccaacttcc ccgtcaacct gctgccgcgg cacgtcaacg | 1620 |
| actcccgctc gccggagcag tactgcaggg agaccgtcat gaccatctgg cactaccacg | 1680 |
| gcggatgcca cgtcggcgcc gtcgtcgacg acaactaccg ggtgttcggg gtgaggggc | 1740 |
| tcagggtgat cgacagctcc accttcaggt actcccccgg caccaacccg caggccaccg | 1800 |
| tcatgatgct cggcaggtaa acgcaagtct gaaatgaccc tcgcaattat actgatctga | 1860 |
| atgaatgaat caactcaact caactaacac aactatgata aatctgtaca ggtatatggg | 1920 |
| cataaagatt caggccgaga gatggaggaa atga | 1954 |

<210> SEQ ID NO 3
<211> LENGTH: 1952
<212> TYPE: DNA
<213> ORGANISM: Triticum aestivum L.

<400> SEQUENCE: 3

| | |
|---|---|
| atggcacttg gccgcgcgag atcgccgacg ctggtgctcg ccgccgcggt ccttggcgcg | 60 |
| ctctgcgtcg tcgcactctc ggaggacggt gcgtgtgttc acctgcatgg tttttctggg | 120 |
| ggttttgcac gtcagctacg tgcgttgtct cttttatcat gatcactgga cgctgtgatg | 180 |
| accaatggtg ccatacgtgt gcagagcaac tggagaacct gcggttcgtg cagcacgcgc | 240 |
| aggacgcgcc gctggtgtcg cactacaact acatcgtggt cggcggcggc acgtccgggt | 300 |
| gcccgctggc ggcgacgctg tcggagcact cgcgggtgct gctgctggag cgcggggcc | 360 |
| tccccctaccg caacatgtcc aaccaggagc acttcacgga tgcgctggcc gacacgtcgc | 420 |
| tggcgtcccc ggcccagcgg ttcgtctcca cggacgcgt ggtgaacgcg cgggcgcggg | 480 |
| tgctgggcgg cgggagctgc ctcaacgccg ggttctacac gcgggccagc aacgagtacg | 540 |
| tgcgcacggc cgggtgggac gccggcctcg tcaactcgtc gtaccggtgg gtggagcgcg | 600 |
| cgctggtgtt ccgccccgac gtgccgccgt ggcaggccgc gctccgggac gcgctgctcg | 660 |
| aggccggcgt caccccgac aacgcgcttca ccttcgacca cgtcacgggg accaagatcg | 720 |
| gcggcaccat cttcgacaac agcgggcagc gccacaccgc ggccgacttc ctccggcacg | 780 |
| cccgccccg gcggctcacc gtcgtgctct acgccacggt gtcgcggatc ctgttcagaa | 840 |
| gccaggaggg ggtgccgtac ccggtggcgt acggggtggt gttcgcggac ccgctggggg | 900 |
| tgcagcaccg ggtgtacctc cgggacggcg ggaagaacga ggtgatactg tcggcgggga | 960 |
| cgctggggag cccgcagctg ctgatgctga cgggcgtggg cccgcaggcg cacctggagg | 1020 |
| cgcacggcat ccaggtgctg gtggaccagc ccatggtcgg gcagggcgtg gccgacaacc | 1080 |
| ccatgaactc ggtcttcatc ccgtcgccgg tgcggtgggg gctctcctg gtgcaggtcg | 1140 |
| tcgggatcac caagtccggc agcttcatcg agggcgtgag cggctccgag ttcggcatcc | 1200 |
| cggtctccga cggcgcccgc cgcctggcca gcttcggcct cttctccccc cagaccgggc | 1260 |

```
agctcggcac gctgccgccg gggcagagga cgccggaggc gctgcagcgc gcggcggagg    1320
cgatgaggcg gctggacagg cgggcgttcc ggggcggctt catcctggag aagatcctgg    1380
ggccggtgtc gacggggcac atcgagctgc gcagcaccga cccgcgcgcc aacccggccg    1440
tgaccttcaa ctactccag gaggcggagg acctggagcg gtgcgtccgg gggatccaga    1500
cgatcgagcg ggtgatccag tcgcgcgcct tctccaactt cacctacgcc aacaccaccg    1560
tcgagtccat cttcaccgac tcggccaact tccccgtcaa cctgctgccg cggcacgtca    1620
acgactcccg ctcgccggag cagtactgca gggagaccgt catgaccatc tggcactacc    1680
acggcgggtg ccacgtcggc gccgtcgtcg acgacaacta ccgggtgttc ggggtgaggg    1740
ggctcagggt catcgacagc tccaccttca ggtactcccc cggcaccaac ccacaggcca    1800
ccgtcatgat gctcggcagg taaacgcaag tctgagatga cccccgcaat tatactgatc    1860
tgaatgaatg aatcaactct actaacacaa ctatgataac tctgtacagg tatatgggca    1920
taaagattca ggccgagaga tggaggaaat ga                                  1952

<210> SEQ ID NO 4
<211> LENGTH: 1746
<212> TYPE: DNA
<213> ORGANISM: Triticum aestivum L.

<400> SEQUENCE: 4
atggcacttg gccgcgcgag atcgccggcg ctggtgctcg ccgccgccgt ccttggcgcg      60
ctctgcgtcg tcgcgctctc ggaggatgag caactggaga acctgcggtt cgtgcagcac     120
gcgcaggacg cgccgctggt gtcgcactac aactacatcg tggtgggcgg cggcacgtcc     180
gggtgcccgc tggcggcgac gctgtcggag cactcgcggg tgctgctgct ggagcgcggg     240
ggcctcccct accgcaacat gtccaaccag gagcacttca cggacgcgct ggccgacacg     300
tcgctggcgt ccccggcgca gcggttcgtg tccacggacg gcgtggtgaa cgcgcgggcg     360
cgggtgctgg gcgcgggag ctgcctcaac gccgggttct acacgcgggc cagcaacgag     420
tacgtgcgca cggccgggtg ggacgccggc ctcgtcaact cgtcgtaccg gtgggtggag     480
cgcgcgctgg tgttccgccc ggacgtgccg ccgtggcagg ccgcgctccg ggacgcgctg     540
ctggaggccg cgtcacccc cgacaacggc ttcaccttcg accacgtcac ggggaccaag     600
atcggcggca ccatcttcga caacaacggg cagcgccaca cggccgccga cttcctccgg     660
cacgcccggc cgcgggggct caccgtggtg ctctacgcca cggtgtcgcg ggtcctgttc     720
aggagccagg aggggtgcc gtacccggtg gcgtacgggg tggtgttcgc ggacccgctg     780
ggggtgcagc accgggtgta cctccgggac gggggcaaga acgaggtgat cctgtcggcg     840
gggacgctgg ggagcccgca gctgctgatg ctgagcggcg tgggcccgca ggtgcacctg     900
gaggcgcaca gcatccaggt gctggtggac cagcccatgg tcgggcaggg cgtggccgac     960
aaccccatga actcggtctt catcccgtcg ccggtgccgg tggggctgtc cctggtgcag    1020
gtcgtcggga tcaccaagtc cggcagcttc atcgagggcg tgagcggctc cgagttcggc    1080
atcccggtgt ccaacggcgc ccgcggggtg gccagcttcg ggctcttctc cccgcagacc    1140
gggcagctcg gcacgctgcc gccggggcag aggacgccag aggcgctgca gcgcgcggcg    1200
gaggcgatgc ggcggctgga caggcgggcg ttcggggcg gcttcatcct ggagaagatc    1260
ctggggccgg tgtcgacggg gcacatcgag ctgcgcagca ccgacccgcg cgccaacccg    1320
gccgtgacct tcaactactt ccaggaggcg gaggacctgg agcggtgcgt ccgggggatc    1380
```

```
cagacgatcg agcgggtgat ccagtcgcgc gccttctcca acttcaccta cgccaacacc    1440
accgtggagt ccatcttcac cgactcggcc aacttccccg tcaacctgct gccgcgccac    1500
gtcaacgact cccgctcgcc ggagcagtac tgcagggaga ccgtcatgac catctggcac    1560
taccacggcg ggtgccacgt cggcgccgtc gtcgacgaca actaccgggt gttcggggtc    1620 aggggggctca gggtcatcga cagctccacc ttcaggtact cccccggcac caacccgcag    1680
gccaccgtca tgatgctcgg caggtatatg ggcataaaga ttcaggccga gagatggagg    1740
aaatga                                                               1746
```

<210> SEQ ID NO 5
<211> LENGTH: 1746
<212> TYPE: DNA
<213> ORGANISM: Triticum aestivum L.

<400> SEQUENCE: 5

```
atggcacttg gccgcgcgag atcaccggcg ctggtgctcg ccgccgccgt tcttggcgcg      60
ctctgcatcg tcgcactctc ggaggatgag caactggaga acctgcggtt cgtgcagcac     120
gcgcaggacg cgccgctggt gtcgcactac aactacatcg tggtcggcgg cggcacgtcc     180
gggtgcccgc tggcggcgac gctgtcggag cactcgcggg tgctcctgct ggagcgcggg     240
ggcctcccct accgcaacat gtcgaaccag gagcacttca cggacgcgct ggccgacacg     300
tcgctggcgt ccccggccca gcggttcatc tccacggacg cgtggtgaa cgcgcgggcg      360 cgggtgctgg gcggcgggag ctgcctcaac gccggattct acacgcgggc cagcaacgag     420
tacgtgcgca cggccgggtg ggacgccggc ctcgtgaact cgtcgtatcg gtgggtggag     480
cgcgcgctgg tgttccgccc cgacgtgccg ccgtggcagg ccgcgctccg ggacgcgctg     540
ctcgaggccg cgtcaccccc cgacaacggc ttcaccttcg atcacgtcac ggggaccaag     600
atcggcggca ccatcttcga caacaacggg cagcgccaca cggccgccga cttcctccgg     660
cacgcccggc ccgggggct caccgtcgtg tctctacgcca cggtgtcccg gatcctgttc     720
agaagccagg aggggtgcc gtatccggtg gcgtacgggg tggtgttcgc ggacccgctg     780
ggggtgcagc accgggtgta cctccgggac gggggggaaga acgaggtgat actgtcggcg    840
gggacgctgg ggagcccgca gctgctgatg ctgagcggcg tcggcccgca ggcgcacctc    900
gaggcacacg gcatccaggt gctggtggac cagcccatgg tcgggcaggg cgtgccgac    960 aaccccatga actcggtctt catcccgtcg ccggtgccgg tggggctctc cctggtgcag   1020
gtcgtcggga tcaccaagtc cggcagcttc atcgagggcg tgagcggctc cgagttcggc   1080
atcccggtct ccgacggcgc ccgccgcctg gccagcttcg gcctcttctc ccccagacc    1140 ggcagctcg gcacgctgcc gccggggcag aggacgccgg aggcgctgca gcgcgcggcg   1200
gaggcgatga ggcggctgga caggcgggcg ttccggggcg ggttcatcct ggagaagatc   1260
ctggggccgg tgtccacggg ccacatcgag ctgcgcagca ccgacccgcg cgcgaacccg   1320
gcggtgacgt tcaactactt ccaggaggcg gaggacctgg agcggtgcgt ccgggggatc   1380
cagacgatcg agcgggtgat ccagtcgcgc gccttctcca acttcaccta cgccaacacc   1440
accgtcgagt ccatcttcac cgactcggcc aacttccccg tcaacctgct gccgcggcac   1500
gtcaacgact cccgctcgcc ggagcagtac tgcagggaga ccgtcatgac catctggcac   1560
taccacggcg gatgccacgt cggcgccgtc gtcgacgaca actaccgggt gttcggggtg   1620 aggggggctca gggtgatcga cagctccacc ttcaggtact cccccggcac caacccgcag   1680
gccaccgtca tgatgctcgg caggtatatg ggcataaaga ttcaggccga gagatggagg   1740
``` aaatga                                                                  1746

<210> SEQ ID NO 6
<211> LENGTH: 1746
<212> TYPE: DNA
<213> ORGANISM: Triticum aestivum L.

<400> SEQUENCE: 6
atggcacttg gccgcgcgag atcgccgacg ctggtgctcg ccgccgcggt ccttggcgcg    60
ctctgcgtcg tcgcactctc ggaggacgag caactggaga acctgcggtt cgtgcagcac   120
gcgcaggacg cgccgctggt gtcgcactac aactacatcg tggtcggcgg cggcacgtcc   180
gggtgcccgc tggcggcgac gctgtcggag cactcgcggg tgctgctgct ggagcgcggg   240
ggcctcccct accgcaacat gtccaaccag gagcacttca cggatgcgct ggccgacacg   300
tcgctggcgt ccccggccca gcggttcgtc tccacggacg gcgtggtgaa cgcgcgggcg   360
cgggtgctgg gcgcggggag ctgcctcaac gccgggttct acacgcgggc cagcaacgag   420
tacgtgcgca cggccgggtg ggacgccggc ctcgtcaact cgtcgtaccg gtgggtggag   480
cgcgcgctgg tgttccgccc cgacgtgccg ccgtggcagg ccgcgctccg ggacgcgctg   540
ctcgaggccg gcgtcacccc cgacaacggc ttcaccttcg accacgtcac ggggaccaag   600
atcggcggca ccatcttcga caacagcggg cagcgccaca ccgcggccga cttcctccgg   660
cacgcccggc cccggcggct caccgtcgtg ctctacgcca cggtgtcgcg gatcctgttc   720
agaagccagg aggggtgcc gtacccggtg cgtacgggg tggtgttcgc ggacccgctg   780
ggggtgcagc accgggtgta cctccgggac ggcgggaaga acgaggtgat actgtcggcg   840
gggacgctgg ggagcccgca gctgctgatg ctgagcggcg tgggcccgca ggcgcacctg   900
gaggcgcacg gcatccaggt gctggtggac cagcccatgg tcgggcaggg cgtggccgac   960
aaccccatga actcggtctt catcccgtcg ccggtgccgg tggggctctc cctggtgcag  1020
gtcgtcggga tcaccaagtc cggcagcttc atcgagggcg tgagcggctc cgagttcggc  1080
atcccggtct ccgacggcgc ccgccgcctg ccagcttcg gcctcttctc cccccagacc  1140
gggcagctcg gcacgctgcc gccggggcag aggacgccgg aggcgctgca gcgcgcggcg  1200
gaggcgatga gcggctgga caggcgggcg ttccggggcg gcttcatcct ggagaagatc  1260
ctgggggccgg tgtcgacggg gcacatcgag ctgcgcagca ccgacccgcg cgccaacccg  1320
gccgtgacct tcaactactt ccaggaggcg gaggacctgg agcggtgcgt ccggggggatc  1380
cagacgatcg agcgggtgat ccagtcgcgc gccttctcca acttcaccta cgccaacacc  1440
accgtcgagt ccatcttcac cgactcggcc aacttccccg tcaacctgct gccgcggcac  1500
gtcaacgact cccgctcgcc ggagcagtac tgcagggaga ccgtcatgac catctggcac  1560
taccacggcg ggtgccacgt cggcgccgtc gtcgacgaca actaccgggt gttcggggtg  1620
agggggctca gggtcatcga cagctccacc ttcaggtact cccccggcac caacccacag  1680
gccaccgtca tgatgctcgg caggtatatg ggcataaaga ttcaggccga gagatggagg  1740
aaatga                                                              1746

<210> SEQ ID NO 7
<211> LENGTH: 581
<212> TYPE: PRT
<213> ORGANISM: Triticum aestivum L.

<400> SEQUENCE: 7

```
Met Ala Leu Gly Arg Ala Arg Ser Pro Ala Leu Val Leu Ala Ala Ala
1               5                   10                  15
Val Leu Gly Ala Leu Cys Val Val Ala Leu Ser Glu Asp Glu Gln Leu
            20                  25                  30
Glu Asn Leu Arg Phe Val Gln His Ala Gln Asp Ala Pro Leu Val Ser
        35                  40                  45
His Tyr Asn Tyr Ile Val Val Gly Gly Thr Ser Gly Cys Pro Leu
    50                  55                  60
Ala Ala Thr Leu Ser Glu His Ser Arg Val Leu Leu Glu Arg Gly
65                  70                  75                  80
Gly Leu Pro Tyr Arg Asn Met Ser Asn Gln Glu His Phe Thr Asp Ala
                85                  90                  95
Leu Ala Asp Thr Ser Leu Ala Ser Pro Ala Gln Arg Phe Val Ser Thr
            100                 105                 110
Asp Gly Val Val Asn Ala Arg Ala Arg Val Leu Gly Gly Gly Ser Cys
            115                 120                 125
Leu Asn Ala Gly Phe Tyr Thr Arg Ala Ser Asn Glu Tyr Val Arg Thr
    130                 135                 140
Ala Gly Trp Asp Ala Gly Leu Val Asn Ser Ser Tyr Arg Trp Val Glu
145                 150                 155                 160
Arg Ala Leu Val Phe Arg Pro Asp Val Pro Pro Trp Gln Ala Ala Leu
                165                 170                 175
Arg Asp Ala Leu Leu Glu Ala Gly Val Thr Pro Asp Asn Gly Phe Thr
            180                 185                 190
Phe Asp His Val Thr Gly Thr Lys Ile Gly Gly Thr Ile Phe Asp Asn
    195                 200                 205
Asn Gly Gln Arg His Thr Ala Ala Asp Phe Leu Arg His Ala Arg Pro
    210                 215                 220
Arg Gly Leu Thr Val Val Leu Tyr Ala Thr Val Ser Arg Val Leu Phe
225                 230                 235                 240
Arg Ser Gln Glu Gly Val Pro Tyr Pro Val Ala Tyr Gly Val Val Phe
                245                 250                 255
Ala Asp Pro Leu Gly Val Gln His Arg Val Tyr Leu Arg Asp Gly Gly
            260                 265                 270
Lys Asn Glu Val Ile Leu Ser Ala Gly Thr Leu Gly Ser Pro Gln Leu
    275                 280                 285
Leu Met Leu Ser Gly Val Gly Pro Gln Val His Leu Glu Ala His Ser
    290                 295                 300
Ile Gln Val Leu Val Asp Gln Pro Met Val Gly Gln Gly Val Ala Asp
305                 310                 315                 320
Asn Pro Met Asn Ser Val Phe Ile Pro Ser Pro Val Pro Val Gly Leu
                325                 330                 335
Ser Leu Val Gln Val Val Gly Ile Thr Lys Ser Gly Ser Phe Ile Glu
            340                 345                 350
Gly Val Ser Gly Ser Glu Phe Gly Ile Pro Val Ser Asn Gly Ala Arg
    355                 360                 365
Arg Leu Ala Ser Phe Gly Leu Phe Ser Pro Gln Thr Gly Gln Leu Gly
    370                 375                 380
Thr Leu Pro Pro Gly Gln Arg Thr Pro Glu Ala Leu Gln Arg Ala Ala
385                 390                 395                 400
Glu Ala Met Arg Arg Leu Asp Arg Arg Ala Phe Arg Gly Gly Phe Ile
                405                 410                 415
Leu Glu Lys Ile Leu Gly Pro Val Ser Thr Gly His Ile Glu Leu Arg
```

```
                420             425             430
Ser Thr Asp Pro Arg Ala Asn Pro Ala Val Thr Phe Asn Tyr Phe Gln
            435                 440                 445

Glu Ala Glu Asp Leu Glu Arg Cys Val Arg Gly Ile Gln Thr Ile Glu
        450                 455                 460

Arg Val Ile Gln Ser Arg Ala Phe Ser Asn Phe Thr Tyr Ala Asn Thr
465                 470                 475                 480

Thr Val Glu Ser Ile Phe Thr Asp Ser Ala Asn Phe Pro Val Asn Leu
                485                 490                 495

Leu Pro Arg His Val Asn Asp Ser Arg Ser Pro Glu Gln Tyr Cys Arg
            500                 505                 510

Glu Thr Val Met Thr Ile Trp His Tyr His Gly Gly Cys His Val Gly
        515                 520                 525

Ala Val Val Asp Asp Asn Tyr Arg Val Phe Gly Val Arg Gly Leu Arg
        530                 535                 540

Val Ile Asp Ser Ser Thr Phe Arg Tyr Ser Pro Gly Thr Asn Pro Gln
545                 550                 555                 560

Ala Thr Val Met Met Leu Gly Arg Tyr Met Gly Ile Lys Ile Gln Ala
                565                 570                 575

Glu Arg Trp Arg Lys
            580

<210> SEQ ID NO 8
<211> LENGTH: 581
<212> TYPE: PRT
<213> ORGANISM: Triticum aestivum L.

<400> SEQUENCE: 8

Met Ala Leu Gly Arg Ala Arg Ser Pro Ala Leu Val Leu Ala Ala Ala
1               5                   10                  15

Val Leu Gly Ala Leu Cys Ile Val Ala Leu Ser Glu Asp Glu Gln Leu
            20                  25                  30

Glu Asn Leu Arg Phe Val Gln His Ala Gln Asp Ala Pro Leu Val Ser
        35                  40                  45

His Tyr Asn Tyr Ile Val Val Gly Gly Gly Thr Ser Gly Cys Pro Leu
    50                  55                  60

Ala Ala Thr Leu Ser Glu His Ser Arg Val Leu Leu Leu Glu Arg Gly
65                  70                  75                  80

Gly Leu Pro Tyr Arg Asn Met Ser Asn Gln Glu His Phe Thr Asp Ala
                85                  90                  95

Leu Ala Asp Thr Ser Leu Ala Ser Pro Ala Gln Arg Phe Ile Ser Thr
            100                 105                 110

Asp Gly Val Val Asn Ala Arg Ala Arg Val Leu Gly Gly Ser Cys
            115                 120                 125

Leu Asn Ala Gly Phe Tyr Thr Arg Ala Ser Asn Glu Tyr Val Arg Thr
130                 135                 140

Ala Gly Trp Asp Ala Gly Leu Val Asn Ser Ser Tyr Arg Trp Val Glu
145                 150                 155                 160

Arg Ala Leu Val Phe Arg Pro Asp Val Pro Trp Gln Ala Ala Leu
            165                 170                 175

Arg Asp Ala Leu Leu Glu Ala Gly Val Thr Pro Asp Asn Gly Phe Thr
            180                 185                 190

Phe Asp His Val Thr Gly Thr Lys Ile Gly Gly Thr Ile Phe Asp Asn
            195                 200                 205
```

```
Asn Gly Gln Arg His Thr Ala Ala Asp Phe Leu Arg His Ala Arg Pro
    210                 215                 220

Arg Gly Leu Thr Val Val Leu Tyr Ala Thr Val Ser Arg Ile Leu Phe
225                 230                 235                 240

Arg Ser Gln Glu Gly Val Pro Tyr Pro Val Ala Tyr Gly Val Val Phe
                245                 250                 255

Ala Asp Pro Leu Gly Val Gln His Arg Val Tyr Leu Arg Asp Gly Gly
            260                 265                 270

Lys Asn Glu Val Ile Leu Ser Ala Gly Thr Leu Gly Ser Pro Gln Leu
        275                 280                 285

Leu Met Leu Ser Gly Val Gly Pro Gln Ala His Leu Glu Ala His Gly
    290                 295                 300

Ile Gln Val Leu Val Asp Gln Pro Met Val Gly Gln Gly Val Ala Asp
305                 310                 315                 320

Asn Pro Met Asn Ser Val Phe Ile Pro Ser Pro Val Pro Val Gly Leu
                325                 330                 335

Ser Leu Val Gln Val Val Gly Ile Thr Lys Ser Gly Ser Phe Ile Glu
            340                 345                 350

Gly Val Ser Gly Ser Glu Phe Gly Ile Pro Val Ser Asp Gly Ala Arg
        355                 360                 365

Arg Leu Ala Ser Phe Gly Leu Phe Ser Pro Gln Thr Gly Gln Leu Gly
    370                 375                 380

Thr Leu Pro Pro Gly Gln Arg Thr Pro Glu Ala Leu Gln Arg Ala Ala
385                 390                 395                 400

Glu Ala Met Arg Arg Leu Asp Arg Arg Ala Phe Arg Gly Gly Phe Ile
                405                 410                 415

Leu Glu Lys Ile Leu Gly Pro Val Ser Thr Gly His Ile Glu Leu Arg
            420                 425                 430

Ser Thr Asp Pro Arg Ala Asn Pro Ala Val Thr Phe Asn Tyr Phe Gln
    435                 440                 445

Glu Ala Glu Asp Leu Glu Arg Cys Val Arg Gly Ile Gln Thr Ile Glu
450                 455                 460

Arg Val Ile Gln Ser Arg Ala Phe Ser Asn Phe Thr Tyr Ala Asn Thr
465                 470                 475                 480

Thr Val Glu Ser Ile Phe Thr Asp Ser Ala Asn Phe Pro Val Asn Leu
                485                 490                 495

Leu Pro Arg His Val Asn Asp Ser Arg Ser Pro Glu Gln Tyr Cys Arg
            500                 505                 510

Glu Thr Val Met Thr Ile Trp His Tyr His Gly Gly Cys His Val Gly
    515                 520                 525

Ala Val Val Asp Asp Asn Tyr Arg Val Phe Gly Val Arg Gly Leu Arg
530                 535                 540

Val Ile Asp Ser Ser Thr Phe Arg Tyr Ser Pro Gly Thr Asn Pro Gln
545                 550                 555                 560

Ala Thr Val Met Met Leu Gly Tyr Met Gly Ile Lys Ile Gln Ala
                565                 570                 575

Glu Arg Trp Arg Lys
    580

<210> SEQ ID NO 9
<211> LENGTH: 581
<212> TYPE: PRT
<213> ORGANISM: Triticum aestivum L.

<400> SEQUENCE: 9
```

```
Met Ala Leu Gly Arg Ala Arg Ser Pro Thr Leu Val Leu Ala Ala Ala
1               5                   10                  15

Val Leu Gly Ala Leu Cys Val Val Ala Leu Ser Glu Asp Glu Gln Leu
            20                  25                  30

Glu Asn Leu Arg Phe Val Gln His Ala Gln Asp Ala Pro Leu Val Ser
        35                  40                  45

His Tyr Asn Tyr Ile Val Val Gly Gly Thr Ser Gly Cys Pro Leu
    50                  55                  60

Ala Ala Thr Leu Ser Glu His Ser Arg Val Leu Leu Glu Arg Gly
65              70                  75                  80

Gly Leu Pro Tyr Arg Asn Met Ser Asn Gln Glu His Phe Thr Asp Ala
                85                  90                  95

Leu Ala Asp Thr Ser Leu Ala Ser Pro Ala Gln Arg Phe Val Ser Thr
                100                 105                 110

Asp Gly Val Val Asn Ala Arg Ala Arg Val Leu Gly Gly Gly Ser Cys
            115                 120                 125

Leu Asn Ala Gly Phe Tyr Thr Arg Ala Ser Asn Glu Tyr Val Arg Thr
        130                 135                 140

Ala Gly Trp Asp Ala Gly Leu Val Asn Ser Ser Tyr Arg Trp Val Glu
145                 150                 155                 160

Arg Ala Leu Val Phe Arg Pro Asp Val Pro Pro Trp Gln Ala Ala Leu
                165                 170                 175

Arg Asp Ala Leu Leu Glu Ala Gly Val Thr Pro Asp Asn Gly Phe Thr
                180                 185                 190

Phe Asp His Val Thr Gly Thr Lys Ile Gly Gly Thr Ile Phe Asp Asn
            195                 200                 205

Ser Gly Gln Arg His Thr Ala Ala Asp Phe Leu Arg His Ala Arg Pro
        210                 215                 220

Arg Arg Leu Thr Val Val Leu Tyr Ala Thr Val Ser Arg Ile Leu Phe
225                 230                 235                 240

Arg Ser Gln Glu Gly Val Pro Tyr Pro Val Ala Tyr Gly Val Val Phe
                245                 250                 255

Ala Asp Pro Leu Gly Val Gln His Arg Val Tyr Leu Arg Asp Gly Gly
                260                 265                 270

Lys Asn Glu Val Ile Leu Ser Ala Gly Thr Leu Gly Ser Pro Gln Leu
            275                 280                 285

Leu Met Leu Ser Gly Val Gly Pro Gln Ala His Leu Glu Ala His Gly
        290                 295                 300

Ile Gln Val Leu Val Asp Gln Pro Met Val Gly Gln Gly Val Ala Asp
305                 310                 315                 320

Asn Pro Met Asn Ser Val Phe Ile Pro Ser Pro Val Pro Val Gly Leu
            325                 330                 335

Ser Leu Val Gln Val Val Gly Ile Thr Lys Ser Gly Ser Phe Ile Glu
        340                 345                 350

Gly Val Ser Gly Ser Glu Phe Gly Ile Pro Val Ser Asp Gly Ala Arg
        355                 360                 365

Arg Leu Ala Ser Phe Gly Leu Phe Ser Pro Gln Thr Gly Gln Leu Gly
    370                 375                 380

Thr Leu Pro Pro Gly Gln Arg Thr Pro Glu Ala Leu Gln Arg Ala Ala
385                 390                 395                 400

Glu Ala Met Arg Arg Leu Asp Arg Arg Ala Phe Arg Gly Gly Phe Ile
                405                 410                 415
```

Leu Glu Lys Ile Leu Gly Pro Val Ser Thr Gly His Ile Glu Leu Arg
            420                 425                 430

Ser Thr Asp Pro Arg Ala Asn Pro Ala Val Thr Phe Asn Tyr Phe Gln
            435                 440                 445

Glu Ala Glu Asp Leu Glu Arg Cys Val Arg Gly Ile Gln Thr Ile Glu
            450                 455                 460

Arg Val Ile Gln Ser Arg Ala Phe Ser Asn Phe Thr Tyr Ala Asn Thr
465                 470                 475                 480

Thr Val Glu Ser Ile Phe Thr Asp Ser Ala Asn Phe Pro Val Asn Leu
                485                 490                 495

Leu Pro Arg His Val Asn Asp Ser Arg Ser Pro Glu Gln Tyr Cys Arg
            500                 505                 510

Glu Thr Val Met Thr Ile Trp His Tyr His Gly Gly Cys His Val Gly
            515                 520                 525

Ala Val Val Asp Asp Asn Tyr Arg Val Phe Gly Val Arg Gly Leu Arg
            530                 535                 540

Val Ile Asp Ser Ser Thr Phe Arg Tyr Ser Pro Gly Thr Asn Pro Gln
545                 550                 555                 560

Ala Thr Val Met Met Leu Gly Arg Tyr Met Gly Ile Lys Ile Gln Ala
                565                 570                 575

Glu Arg Trp Arg Lys
            580

<210> SEQ ID NO 10
<211> LENGTH: 25
<212> TYPE: DNA
<213> ORGANISM: Artificial Sequence
<220> FEATURE:
<223> OTHER INFORMATION: primer 1 of the TaMS7-A gene for RT-PCR

<400> SEQUENCE: 10
atactgacac aagtttatgg ggctg                                    25

<210> SEQ ID NO 11
<211> LENGTH: 25
<212> TYPE: DNA
<213> ORGANISM: Artificial Sequence
<220> FEATURE:
<223> OTHER INFORMATION: primer 2 of the TaMS7-A gene for RT-PCR

<400> SEQUENCE: 11
aattacattc aaatatggct ccttg                                    25

<210> SEQ ID NO 12
<211> LENGTH: 22
<212> TYPE: DNA
<213> ORGANISM: Artificial Sequence
<220> FEATURE:
<223> OTHER INFORMATION: primer 3 of the TaMS7-B gene for RT-PCR

<400> SEQUENCE: 12
ggcctcgtga actcgtcgta tc                                       22

<210> SEQ ID NO 13
<211> LENGTH: 25
<212> TYPE: DNA
<213> ORGANISM: Artificial Sequence
<220> FEATURE:
<223> OTHER INFORMATION: primer 4 of the TaMS7-B gene for RT-PCR

<400> SEQUENCE: 13

```
tgaattacat gcaaatttgg ctccg                                           25

<210> SEQ ID NO 14
<211> LENGTH: 23
<212> TYPE: DNA
<213> ORGANISM: Artificial Sequence
<220> FEATURE:
<223> OTHER INFORMATION: primer 5 of the TaMS7-C gene for RT-PCR

<400> SEQUENCE: 14
atgtccaacc aggagcactt cac                                             23

<210> SEQ ID NO 15
<211> LENGTH: 24
<212> TYPE: DNA
<213> ORGANISM: Artificial Sequence
<220> FEATURE:
<223> OTHER INFORMATION: primer 6 of the TaMS7-C gene for RT-PCR

<400> SEQUENCE: 15
gcacagtttt ttgaagcaat gttg                                            24

<210> SEQ ID NO 16
<211> LENGTH: 2601
<212> TYPE: DNA
<213> ORGANISM: Triticum aestivum L.

<400> SEQUENCE: 16
tgactctgtc catcctgaac caaaagaatg ggaaacactt gactaaaact tcaggttcaa     60
ctctccttag caagtaccag tgctactgat atgtgtgatt caagcagcta gtttttgtaa    120
cctcatgatg attacagttg atcttacttt tgtggtgatc acaggtctct tcatatgtga    180
tggcggatgg ggttggccta actttcttgc tctcaagaaa ctcaagaaag gctatgttgt    240
agggtcgagc tgcattgtga aggcagatct cactatcgtt ggtttatcca atgatggcta    300
gatctttacc tcatgccgat ggagataaag ccctttcatc ctcctagcaa gacttatata    360
tgagataatg ttgtggtagc agcactaaaa acttgtgggg tgattagtag taatgagctg    420
gatttgagaa gtgagatgac ttcacgcata tatttctagg tattatatat caagcagaaa    480
tatgttattg gaagtacttg agtttgcatg gatgatgcaa ctatgtcggt cagcttgtct    540
cgctacatgg atgtttgatt cagctgaacc atgttatctc tcgcttggtt tttgtgcacc    600
atggatgtcc ccagttgatg aatcttatgg ttccatgtaa agcactttgc ttctatttat    660
tttgagaagg aaaacggctc ttcccttgtc caccgtccat ttattttgat cccatggtcc    720
aggttttaga actcctagtc ccggaaataa acaactatct tgcaagtgct tcatgtacaa    780
ttgcaacgat gagcaggtga ctaacctaat actccctccg tttctaaata tttgtctttc    840
tagatatttt aacaagtgac tacatacgga gcaaaatgag tggatctaca ctctaaaata    900
tgtctacgta catccgtata tagtagccat ttgaaatgtc tagaaagaca aatatttagg    960
aacagaggga gtatttatta tacttttata aagaatgttg gagtacccat ctctggggag   1020
cctctgcgtg tgaaaatgtc ctccgcgctg tttgttgcac gttggccacc gcggctggc    1080 tccctggggc gctccgggcc atcgatctag gcggccgcct cgcacccgga ctgcttgcct   1140
ctgggtccat gacgaggggg tgcgggcgcg gttggatcca tcgtgatgtg gtgttttgg    1200 tcacaccagt ttgtgccctc ttgttggttg tcctgcgcgt gatgggccga ccgaatctgc   1260
ctgtctgtcg tgttgaccac ccgcggctag ctccctgggg cgctccgggc cattgatcta   1320
ggcagccgcc tcgcacctgg actgcttgcc tctgggtcca tgacgagggg tgcgggtgca   1380
```

```
gtcggatcca tcgtgatgtg gtgttttcgg tcacaccagt ttgtgccctc ttgttgattg   1440
ccctgcgcgt gatgggctga ccggatctgc ctgttagtgt tgtgttggcc acccgcggct   1500
ggctccttgg ggcgctccag gtcatcgatc taggcggtcg cctcgcaccc ggactgcttg   1560
cctctgggtc catgacgaga ggatgcgggc gcggtcggat ccatcatgat gtggtgtttt   1620
cggtcacacc agtttgtgct ctcttgttgg ttgtcctgcg cgtgatgggc cgaccggatc   1680
tgcctgtcag tgttgtgttg gccacccgcg gctggctcct ggggcgctc cgggctatcg   1740 atctaggcgt ccgcctcgca cccggactgc ttgcctctgg gtccatgacg aggaggtgcg   1800
gacgcggtcg gatccatcat gatgtggtgt tttcggtcac accagtttat gccctcttgt   1860
tggttgatct gcgcgtgatg ggccgactag atctgcctgt cagtgttgtg ttggccaccc   1920
gcggctggct ccatggggcg ctccgcgcca tcgatctagg gggccgcctc gcatccagac   1980
tgcttcagga actgacatcc gttcatttat tttgtcagtt catttatttg aggcaaattt   2040
cttcaggaac tgacatccgt tccatggggc atacgttggg gattggtttc tggcgaacgt   2100
tcgccagatt atctttaccg cttttttta gtttctaggt ttttcttggt attttattat   2160
tttcttatag tttggaccga tctccttaca tcatagtttt gccttggtac ctgtaatatg   2220
tatttgtgct tgtatataaa aatggaggga gtatagtttt tcgggaaaaa atatagtgca   2280
cgcgcaaaac cgtctcaaga tcggccagta aaccctcccc cttgctgctt catcgcattt   2340
gatatgatat actcaacagc tcctcccgtc taaaaagaaa gttcatcact tctgcatttc   2400
acaaccgatg cattccattt gatataacca ttccctttct atactgacac aagtttatgg   2460
ggctgttctt tgcactgcaa ccgcctccgc attatttaac acatctaccc tcgatctacc   2520
cgcgcgctaa ctcgaggttt ataaaccaag cgaacttttc gcgtccctga agcgcaaagg   2580
atgccgagct cgccggcgca a                                              2601
```

<210> SEQ ID NO 17
<211> LENGTH: 2635
<212> TYPE: DNA
<213> ORGANISM: Triticum aestivum L.

<400> SEQUENCE: 17

```
tgctgccaaa gaagaatgga gctttggagg tcaaccatta tcgaccaatc agcttgatcc     60
actctgttgc taagctaatc tccaaagtgc tcgttgcaag gctggcaggg gccctggata    120
aaatcatctc accggcgtag actgcatttc agaaaggcaa atgcagccac gagagctatc    180
agtacgtgca aagctgcgtt cggatgttac ataggacgaa gaaaaaggca ttttcttca    240 aactcgacat agcaaaggct tttgattcgg tgacatggga ggacttgctc gagctcaagc    300
aaaaaaatgg gttccctcc tagatgggga aactggatag cgctgctact ctcttctacc    360
acctcctcct gcttgctcaa cgaaacgcag agccaatcaa tatctcatgg ttgtggcttt    420
aggcagggtg attcgctatc cctgctgctt ttcatcctgg cgatcgaccc tcttcaccac    480
ctccttcaag ctgctgcaga ggaagagatg atcgctcagc tgacaggccg tgggatcagc    540
atgtggatta gcttatacgc tgatgacgcc gtcattttcg ccaacccggt gaaggaagaa    600
gtggacacgc tgttgttttt gctcagcaga ttcggggagg ccacgggact gaagttaaac    660
caggcaaaat ctgaagtcat cccaattaac tgtgctgatg ttcagttaac tgaggttctg    720
caaaactttg gggggctgca gtccacgttc ccaaccacat acctgggact gccaatctct    780
ccaaggaagc taaggctggt gcatttccaa tttatcattg accggatacg ctcaaggttg    840
```

```
gctggttgga aaggcaagct gatgaacatg gcaggtagaa gggtactggt gcgtgctgtg      900
ttgatggcac tgccggtgtt tgcaatgaca gtactcaaag tgccgaagaa gattttaaaa      960
gaggtggaaa aagcaaggag gcagtttcta tgggcacatg atgagaatgt cactggcgcc     1020
aaatgcaagg tggcctgggg caaagtctgt cttccggtgg ccaagggggg gctaggtttg     1080
ttggacctcc atcgtttcag cacagctctc cggctgcgct ggttgtggct ctcctggcaa     1140
cagccacacc ggccctggat gaacttcccg gcccaaggag gacctggagc tgtttgcatc     1200
ggccaccttt gtgcacttgg gcaacggaaa aacagcgcgt ttctggactt gcaaatggat     1260
ctgggcggtg gcgctgcaac acgagttccc atcattgttt cagcatgcca gaagaaaaaa     1320
caggatggtt catgatgcgc tgacaaatga cacatgggta cgtgatctcc ggcatggcaa     1380
catagtagag attgctcacc ggttttttgca aatgtggaga agattcagg gtgcaggcat     1440
tgttctctcc tccaacgagg accggatcag ctgggtggca accagaggag gaggaagcta     1500
ctcggctaag gctgcttacg atctacaaat cagtgacatt cctccttcag gaggcaaagc     1560
tgcgatttgg agggcttggg cgccaggcac ggtgaagatc ttcgcctggc tgctccacca     1620
ggacaagctt tggtgcaacg atcgcctgca acggcgaggg tggcccaatg ggtatttttg     1680
cgtatgctgc aacagaaatc tggaaagctc aatacacctt ttctgggact gcccttttgc     1740
ccgatctgtc tggccggcag tgtcgcgtag atatggttgc gctgtgctca agaagcgcg     1800
ggacgcaggt cacagttccc tcagacattg gaaagactg accgcactaa cgcctcaaag     1860
ttgcagaaaa gggctaaggt cgatgctgtt gctgatcact tgggagtttt ggaaagagag     1920
gaacgcgtgt gtatttagag gaaaaacgcc ccagacggag gatgttcagc gagccatcaa     1980
gaacacgatg gagctctggc gggcagcagg agctcgatgc attgaggccc tgttctgtag     2040
cgagataaaa cgtacggctc atgtagctgg cctagttttg gccattctta gctcttctca     2100
aaccatgatc acttgatcgc ccatgtattt cccactgctt tcttctaaat caatgaagca     2160
ggtgaacccg gatctttcaa aaaaaaacct cctgatgtac tcagtgtcgt ggccggtgat     2220
ttaaccgtgt ccactgatta attggaatgt atggtgttcc aggtcaaaaa agaatgtcaa     2280
atgtaattct ttcggaaaaa atatagtgca cgcgcaaaac cgtctcaaga ttggccagta     2340
aaccctctcg cttgctgctc cgtcgcattt gatatactca acagctcctc ctgtctaaaa     2400
agaaagttca tcacttctgc atttcacgac caatgcattg catttgatat aaccattccc     2460
tttctatagt aacacatgtt tatgggctcc tcgcggctct tctttgcact gcaaccgcct     2520
ccgcattatt taacacatct accctcgatc tacccgcgcg ctaactccag gtttataagc     2580
gaagcgaact tttcgcgtcc ctgaagcgta aaggatgccg agctcgccgg cgcaa          2635
```

<210> SEQ ID NO 18
<211> LENGTH: 2821
<212> TYPE: DNA
<213> ORGANISM: Triticum aestivum L.

<400> SEQUENCE: 18

```
ctgacatagt acatgtaatc tttaaatcca taaccttctg tttctatcag tgctactagg       60
ttgtaaaatg ttatgtctga caccatcata gatctctcaa tgttgtctct gtcatggaaa      120
tgcatcctca attcccaaac ctcatcatcc agactgcaaa taatataaag cactaatgaa      180
acactaataa aactaataac caaatgtaaa ccctagggca caggacaaac aaagcacaac      240
atcagaacta atctaaaaat gtcaacccta ggcacaggac aaacaaagca cataatctga      300
actaatctaa ataatgtcct agggcacatg acaacaaaat cacaacattt gacacttgta      360
```

```
ctgcatttga taggatagaa caatatgaac actaaccta gggtaccct cgcaacacaa      420 ttgaatggag taccctggca acgcaattga atggagaacg ggaagggaag agcaaagaaa    480
agtggatctc actatacgcc gccgaaggat gacgcgatgt gctggcttcc cgtcgaattg    540
gccttcaccg ccgcggcgaa tgctctggcc gccctgtatt ccatcgaata ttgcgggtcc    600
tcctcctcct cttcctctga cggcttgcta gggttcgaac tcgcgcacag ctcgcctaga    660
tccactgcgg gtcctcctcc actacgtacg atgcgtgcgg cgctgccggg cggagagccg    720
ccaccagcat ctccaccttt cgccggactg cgcatctctg tgtttctatg gaatggcgac    780
ggcaccaatg ggggagggcg acggcagcgg gagcgaggag gaggggaag aagaatgggg     840 gagggcgacg gcggcgggag cgaggaggag ggggaagaag aatggggag ggcgacggcg     900 gcgggagcga ggaggagggg gaagaagaat ggggagggc gacggcggcg ggagcgagga    960
gggggaaaag agacggatgc gggagtggat gactaaagac gagccctaac ggcgccgtct   1020
aacgccgact gccggctgtc gggacggcct ggagtgccat gtaggcgaaa acgggccca    1080 acctgtcata aactcactta acacggcccg atccgccgat cagtggtttt tgcaaaacaa   1140
ttacgataga cgtggtgctt tctgcaacaa ttctgtaacc taatgttttc cgcaaaccta   1200
gccctcaaag tggtggtttt atgcaattta ctctgattac agttgatctt acttttgtgg   1260
tgatcacagg tctcttcgta tgtgatggcg gatggggttg gcctaacttt cttggactca   1320
agaaactcaa gaaaggctat gttgtagggt cgagctgcat tgtgaaggca gatctcacta   1380
tcgttggttt atacaatgat ggctagatct ttacctcatg cctatggaga gataaagccc   1440
tttcatcctc ctagcaagac ttatatatga gatgatgttg tggtagcagc actaaaaact   1500 tttttttag aaaaggagca gcactaaaaa cttggggtga ttagtagtaa tgagctggat    1560
ttgagaagtg agatgacttc acgcatatat ttctaggtat tatatcaa gcagaaatat    1620 gatattggaa gtacttgtgt ttgcatggat gatgcaacta tgtcggtcag cttgtctcgc    1680
tacatggatg tttgattcag ctaaaccatg ttatctctcg cttggttttt gtgcaccatg   1740
gatgttccag ttgatgaatg gttccatgta aagcgctttg cttctattta ttttgggaag   1800
gaaaacggct cttccattg tccaccgtcc attatttg atcccatggg ccagatttta      1860
gaactcccgg tcccggaact aaactaatat ttattacttc tataaagaat gttggagtat   1920
caggtcttcg gggagccttt gcgtgtgaaa atgtcctccg cgttgttcgt tgcatgttgg   1980
ccacccgcgg ttggctccct ggggcgctct gggccgtccg atctaggcag gcgcctcaca   2040 cccgacgac ttgccatgg gtccatgccg gggggctgc gggcacggtt gggtccatcg       2100
tgatgtggtg ttttcgatca caccagtttg tgccctcttg ttggttgcct tgcgcgtgac   2160
gggccgaccc tgttggtgta gttcgcttgt gccaggcaag ccgcgcacac ccccggatcg   2220
gggtggcgcg tgttaggaaa ccggagaggg ccatccggcc agccgtcgcg atggcgggcc   2280
agccggccaa ggttcattta tttgaggcaa atttctttag tgacatccgt gctatgggc    2340 gtttgctggg gattggtttc tagcgaacgt tcgccagatt atctttaccg cttctcttta   2400
gtatctaggt ttttcttagt attttattat ttttctcata gtttggaccg atctcctcac   2460
gtcagaatgt caaatgtaat cctttcgaaa aaaatatagt gcacgcgcga aaccgtctc    2520 aagattggcc agtaaaccct cctgcttact gctccatcgc atttgatata ctccttctgt   2580
gtaaaaagaa tgttcatcac ttttgcattt cacaaccaat gcattgcatt tgatataacc   2640 attcccttc tatagtaaca caagtttatg ggctcctcgc agctgttctt tgcactgcaa    2700
```

```
ccgcctccgc attatttaac agatctaccc tcgatctacc cgcgcgctaa ctcgaggttt    2760
ataaaccaag cgaactttc gcgtccctga agcgcaaagg atgccgagct cgccggcgca    2820
a                                                                   2821
```

<210> SEQ ID NO 19
<211> LENGTH: 40
<212> TYPE: DNA
<213> ORGANISM: Artificial Sequence
<220> FEATURE:
<223> OTHER INFORMATION: Primer 7

<400> SEQUENCE: 19

```
aagcttctga catagtacat gtaatcttta aatccataac                            40
```

<210> SEQ ID NO 20
<211> LENGTH: 25
<212> TYPE: DNA
<213> ORGANISM: Artificial Sequence
<220> FEATURE:
<223> OTHER INFORMATION: Primer 8

<400> SEQUENCE: 20

```
ggatccttgc gccggcgagc tcggc                                            25
```

<210> SEQ ID NO 21
<211> LENGTH: 20
<212> TYPE: DNA
<213> ORGANISM: Triticum aestivum L.

<400> SEQUENCE: 21

```
ctggtggacc agcccatggt                                                  20
```

<210> SEQ ID NO 22
<211> LENGTH: 1453
<212> TYPE: DNA
<213> ORGANISM: Triticum aestivum L.

<400> SEQUENCE: 22

```
tatttcaagg agccatattt gaatgtaatt catggcataa tattgtatttt ggggaacctg    60 gtttagacag attaatttgt ttttttccac ttattctcta ggcatagtct tttagtgcct    120
gtttgttgat tattatgaaa cccagtcatc cctttaacat gcatttctct gcattgcaaa    180
ataagaagga aaaacttatg ttgcaaaggc atgacggtgg ttcaagcaac aatacttcga    240
tcaaaaaaat tggaaaccgg ttgccacatc cacctaccaa tttccattga taacaagagt    300
agcaaaccag aatactgtgc aggatgcatt tacagttttg tactagaaac ttaatttcat    360
gaaattacat accactattt tacttggtgg ttgttacatg ctacaaacgc caggttccct    420
tcagagggat ccagcaagcc atcatcttat ctatacaggg accgagtaca tgtcaaagga    480
acatgatgag ttaagaatgg aacagccaaa ggcagaaatg acttgaacat tttttttcct    540
tgtttccaac ttgccctact tgcctgctac ctatatattg gcttgcgaaa ttctctccct    600
acctatgtta tcaggaacca gaaaatgcta cttcggcatc tctgttgtcc agaatacccca   660 agaagtcacc aacaattgca tgcttgcata agaataattc atatagtgag gttttcttgg    720
atggccgtga aggagccaca aatgtttccg cccatgtctg ggaatgtcgc acatcctggc    780
aagggtttca ccttgccttt acggtcaaca cttacagggt acttgaggag gtggcctctc    840
atctcagtca cctcatttgc aaagaactga tcccagttat gttgcccgag ttgacgaacc    900
cgcctcatgc actctaggct ctctggatgg ttaaagtctt cctcgataat tccaatatgc    960
```

```
tcagcccaga gggacattct gtagccataa atctacataa aaaatcacca aacttgattt    1020
aagagtataa tccagaaata ccagctgcgt cataactaga ttattaccct aagagatgag    1080
atgatatacc ccgacaacct ttttcacttg ctgttttaga atgcacatat tagtatttat    1140
attcacataa ctgtacttgt agaattgcca ccaacagtat ttatgtgtca ttacatgtct    1200
atagtttagt gtatatataa ttgaaaaaaa ggtaaatgtt aaatgggtgt agttggaggc    1260
agtctctcta ataaggtga aacaattgta atgaagcagc agttctaagc aacgcataac     1320
atcaggaaga caagtacaaa atctgcaggc acaatctcaa aatgcaagct catgaaaaca    1380
cctgtcttct gcaggtacca aaagatgtga ttcagcagct tgaacttgaa acatgaggca    1440
ttacctgtcc acg                                                      1453

<210> SEQ ID NO 23
<211> LENGTH: 1446
<212> TYPE: DNA
<213> ORGANISM: Triticum aestivum L.

<400> SEQUENCE: 23
tatttcacgg agccaaattt gcatgtaatt catggcataa tattgtattt gggggacctg      60
gtttagaaca gattaatttg gttttccac ttattctcta ggcatagtct tttagtgcct     120
gtttgttgat tattatgaaa cccatacatc cctttaacat gcattctct gcactgtaaa      180 ataagaagga aaacttatgt cccaaaggca tgatggtggt tcaagcaaca atacttcggt     240
aaaaaaatgg aaccggttgc cacatccacc caccaatttc cattgatgac aagaggagca     300
aaccaaggcc caacattgct tcagaatagt gtgaaggatg catttacagt tttgcactag     360
aaactttgtt tcatcaaatt acatataaca tactactatt tctcttggtg gttgtcactt     420
gctacaaacg ccaggttccc ttcagaggga tccagcatgt aatcatctta catatacagg     480
gaccgaatac atgtaaaagg aacatgatta gttaagatgg gaacaaccaa aaggcagaaa     540
tgacttgatt tttttttcct tgtttccaac ttgccctact tgcctgctac ctacatattg     600
gcttgcgaaa ttctctccct acctatgtta tcaggaacca gaaagtgcta cttcggcatc     660
tctgttgtcc ataatacca agaagtcacc aacaattgca tgcttgcata agcagaattc      720
atattgtgag gttttcctgg atggccgtga aggagccaca aatgtttccg cccatgtctg     780
ggaatgtcgc acatcctggc aagggtttca ccttgccttt acggtcaaca cttacagggt     840
acttgaggag gtggcctctc atctcagtca cctcatttgc aaagaactga tcccagttat     900
gttgcccgag ttgacgaacc cgcctcatgc actctaggct ctctggatgg ttaaagtctt     960
cctcgataat tccaatatgc tcagcccaga gggacattct gtagccataa atctacataa    1020
aaaatcacca aacttgattt agagtataat ccagaaatac cagctgcgtc ataagtcata    1080
actagattat taccctaaga gatgagataa tatacccaga caacctttt cactgctgtt     1140 ttagaatgca catattagta tttaattcac ataagaactg tacttgtaga attgccacca    1200
acagtatgta tgtgtcatta cgtgtctata gtttagtgta tataaatta aaaaaggta     1260 aatgttaaat gggcgtagtt ggaggcagtc tctctgaaaa cgtaaaaaat aagtaaggtg    1320
aaacaattgt aatgaagcag tggttctaag caacgcataa catcaggaag acaagtacaa    1380
aatctgcagg cacaatctca aaatgcaagc tcatgaaaac acctgtcttc tgcaggtacc    1440
aaaaaa                                                               1446

<210> SEQ ID NO 24
```

```
<211> LENGTH: 1472
<212> TYPE: DNA
<213> ORGANISM: Triticum aestivum L.

<400> SEQUENCE: 24
tatttcacgg agccaaattt gcatgtaatt cgtggcataa tattgtattt gggggacctg      60
gtttagaaca gattaatttg gttttttccac ttattctcta ggcatagtct tttagtgcct    120
gtttgttgat tactatgaaa cccagacatc cctttaacat gcatttctct gcattgcaaa     180
ataagaaaga aaacttatgt tgcaaaggca tgatggtggt tcaagcaaca atacttcggt     240
aaaaaaatgg aaaccggttg caacatccac ccaccaattt ccattgatga caagagtagc    300
aaaccaaggc ccaacattgc ttcaaaaaac tgtgcaggat gcatttacag ttttgcacta   360
gaaacttagt ttcatcaaat tacatataac atactactat ttctcttggt ggttgtcact    420
tgctacaaac gccaggttcc cttcagaggg atccagcatg taatcatctt acctatacag    480
ggaccgaata catgtaaaag gaacatgatt agttaagacg ggaacaacca aaaggcagaa    540
atgacttgaa tttttttttcc ttgtttccaa cttgccctac ttgcctgcta cctacatatt   600
ggcttgcgaa attctctccc tacctatgtt atcaggaacc agaaagtgct acttcggcat    660
ctctgttgtc cagaatacccc aagaagccaa caattgcatt cttgcataag cagaattcat   720
attgtgaggt tttcctggat ggccgtgaag gagccacaaa tgtttccgcc catgtctggg    780
aatgtcgcac atcctggcaa gggtttcacc ttgcctttac ggtcaacact tacagggtac    840
ttgaggaggt ggcctctcat ctcagtcacc tcattggcaa gaactgatc ccagttatgt     900 tgcccgagtt gacgaacccg cctcatgcac tctaggctct ctggatggtt aaagtcttcc    960
tcgataattc caatatgctc agcccagagg gacattctgt agccataaat ctacataaaa   1020
gatcaccaaa cttgatttag agtataatcc agaaatacca gctgcgtcat aactagatta   1080
ttaccctata agagatgaga tgatataccc cgacaacctt tttcacttgc tgttttagaa   1140
tgcacatatt agtatttata ttcacataag aactgtactt gtataattgc caccaacagt   1200
atttatgtgc cattacgtgt ctatagttta gtgtatatat aataaaaaag ggtaaatgtt   1260
aaataggtgt agttggaggc agtctctctg aaaacgtaaa aaataagtta aaacaattgt   1320
aatgaagcag cggttctaag caacgcataa catcaggaag acaagtacaa aatctgcagg    1380
cacaatctca aaatgcaagc tcatgagaac acctgtcttc tgcaggtacc aaaaaatgtg   1440
attcagcagc ttgaacttga aacatgaggc at                                  1472

<210> SEQ ID NO 25
<211> LENGTH: 1487
<212> TYPE: DNA
<213> ORGANISM: Zea mays

<400> SEQUENCE: 25
atggcggcga caatggcagt gacgacgatg gtgacgagga gcaaggagag ctggtcgtca     60
ttgcaggtcc cggcggtggc attcccttgg aagccacgag gtggcaagac cggcggcctc    120
gagttccctc gccgggcgat gttcgccagc gtcggcctca acgtgtgccc gggcgtcccg    180
gcggggcgcg acccgcggga gcccgatccc aaggtcgtcc gggcggcctg cggcctggtc    240
caggcacaag tcctcttcca ggggtttaac tgggagtcgt gcaagcagca gggaggctgg    300
tacaacaggc tcaaggccca ggtcgacgac atcgccaagg ccggcgtcac gcacgtctgg    360
ctgcctccac cctcgcactc cgtctcgcca caaggctaca tgccaggccg cctatacgac    420
ctggacgcgt ccaagtacgg cacggcggcg gagctcaagt ccctgatagc ggcgttccac    480
```

```
ggcaggggcg tgcagtgcgt ggcggacatc gtcatcaacc accggtgcgc ggaaaagaag      540
gacgcgcgcg gcgtgtactg catcttcgag ggcgggactc ccgacgaccg cctggactgg      600
ggccccggga tgatctgcag cgacgacacg cagtactcgg acgggacggg gcaccgcgac      660
cgggcgaggg gttcgcggcg cgcccgaca tcgaccacct caacccgcgc gtgcagcggg      720
agctctccgc ctggctcaac tggctcaggt ccgacgccgt ggggttcgac ggctggcgcc      780
tcgacttcgc caagggctac tcgccggccg tcgccagaat gtacgtggag agcacggggc      840
cgccgagctt cgtcgtcgcg gagatatgga actcgctgag ctacagcggg gacggcaagc      900
cggcgcccaa ccaggaccag tgccggcagg agctgctgga ctggacgcgg gccgtcggcg      960
ggcccgccat ggcgttcgac ttccccacca agggcctgct gcaggcgggc gtgcaggggg     1020
agctgtggcg gctgcgcgac agctccggca acgcggccgg cctgatcggg tgggcgcccg     1080
agaaggccgt caccttcgtc gacaaccatg acaccgggtc gacgcagaag ctctggccgt     1140
tcccatccga caaggtcatg cagggctacg cctacatcct cacccatcca ggagtccccg     1200
gcattttcta cgaccacatg ttcgactgga acctgaagca ggagatatcc acgctgtctg     1260
ccatcagggc gcggaacggc atccgcgccg gagcaagct gcggatcctc gtggcggacg     1320
cggacgcgta cgtggccgtc gtcgacgaga aggtcatggt gaagatcggg acaaggtacg     1380
gcgtgagcag cgtggtcccg tcggatttcc accggcggc gcacggcaag gactactgcg     1440
tctgggagaa agcgagcctc cgcgtcccgg cggggcgcca cctctag                 1487

<210> SEQ ID NO 26
<211> LENGTH: 2736
<212> TYPE: DNA
<213> ORGANISM: Zea mays

<400> SEQUENCE: 26
tgcaccggac actgtctggt ggcataccag acagtccggt gtgccagatc agggcaccct       60
tcggttcctt tgctcctttg cttttgaacc ctaactttga tcgtttattg gtttgtgttg      120
aacctttatg cacctgtgga atatataatc tagaacaaac tagttagtcc aatcatttgt      180
gttgggcatt caaccaccaa aattatttat aggaaaaggt taaaccttat ttcccttcca      240
atctccccct ttttggtgat tgatgccaac acaaaccaaa gaaatatata agtgcagaa      300 ttgaactagt ttgcataagg taagtgcata ggttacttag aattaaatca atttatactt      360
ttacttgata tgcatggttg ctttcttta ttttaacatt ttggaccaca tttgcaccac      420
ttgttttgtt ttttgcaaat cttttggaa attcttttc aaagtctttt gcaaatagtc      480
aaaggtatat gaataagatt gtaagaagca ttttcaagat ttgaaatttc tccccctgtt      540
tcaaatgctt ttcctttgac taaacaaaac tccccctgaa taaaattctc ctcttagctt      600
tcaagagggt tttaaataga tatcaattgg aaatatattt agatgctaat tttgaaaata      660
taccaattga aaatcaacat accaatttga aattaaacat accaatttaa aaaatttcaa      720
aaagtggtgg tgcggtcctt tgctttggg cttaatattt ctcccccttt ggcattaatc      780
gccaaaaacg gagactttgt gagccattta acttttctcc ccattggtaa atgaaatatg      840
agtgaaagat tataccaaat ttggacagtg atgcggagtg acggcgaagg ataaacgata      900
ccgttagagt ggagtggaag ccttgtcttc gccgaagact ccatttccct ttcaatctac      960
gacttagcat agaaatacac ttgaaaacac attagtcgta gccacgaaag agatatgatc     1020
aaaggtatac aaatgagcta tgtgtgtaat gtttcaatca aagtttcgag aatcaagaat     1080
```

| | | | | |
|---|---|---|---|---|
| atttagctca | ttcctaagtt | tgctaaaggt | tttatcatct | aatggtttgg taaagatatc | 1140 |
| gactaattgt | tctttggtgc | taacataagc | aatctcgata | tcaccccttt gttggtgatc | 1200 |
| cctcaaaaag | tgataccgaa | tgtctatgtg | cttagtgcgg | ctgtgttcaa cgggattatc | 1260 |
| cgccatgcag | atagcactct | cattgtcaca | taggagaggg | actttgctca atttgtagcc | 1320 |
| atagtcccta | aggttttgcc | tcatccaaag | taattgcaca | caacaatgtc ctgcggcaat | 1380 |
| atacttggct | tcggcggtag | aaagagctat | tgagttttgt | ttctttgaag tccaagacac | 1440 |
| cagggatctc | cctagaaact | gacaagtccc | tgatgtgctc | ttcctatcaa ttttacaccc | 1500 |
| tgcccaatcg | gcatctgaat | atcctattaa | atcaaaggtg | gatcccttgg ggtaccaaag | 1560 |
| accaaattta | ggagtgtaaa | ctaaatatct | catgattctt | tcacggccc taaggtgaac | 1620 |
| ttccttagga | tcggcttgga | atcttgcaca | catgcatata | gaaagcatac tatctggtcg | 1680 |
| agatgcacat | aaatagagta | aagatcctat | catcgaccgg | tataccttt ggtctacgga | 1740 |
| tttacctccc | gtgtcgaggt | cgagatgccc | attagttccc | atgggtgtcc tgatgggctt | 1800 |
| ggcatccttc | attccaaact | tgttgagtat | gtcttgaatg | tactttgttt ggctgatgaa | 1860 |
| ggtgccatct | tggagttgct | tgacttgaaa | tcctagaaaa | tatttcaact tccccatcat | 1920 |
| agacatctcg | aatttcggaa | tcatgatcct | actaaactct | tcacaagtag atttgttagt | 1980 |
| agacccaaat | ataatatcat | caacataaat | ttggcataca | aacaaaactt tgaaatggt | 2040 |
| tttagtaaag | agagtaggat | cggctttact | gactctgaag | ccattagtga taagaaaatc | 2100 |
| tcttaggcat | tcataccatg | ctgttggggc | ttgcttgagc | ccataaagcg cctttgagag | 2160 |
| tttataaaca | tggttagggt | actcactatc | ttcaaagccg | agaggttgct caacatagac | 2220 |
| ctattcaccc | catttgatca | ctttttggt | ccttcaggat | ctaatagtta tgtataattt | 2280 |
| agagtctctt | gtttaatggc | cagatatttc | taattaatct | aagaatttat gatatttttt | 2340 |
| aatttttat | catgtctgat | gagaattaac | ataaaggctc | aattgggtcc tgaattaata | 2400 |
| atagagtgaa | aattaatcca | gaggctctat | tagaaccttc | aattagtaat accaagatat | 2460 |
| atataagata | gtagagtata | gtttaaatgt | tggcattgtt | cattctttct tttgttattt | 2520 |
| aatttatgct | ttccacggtg | gttagtggtt | acttctgaag | ggtccaaata atgcatgaag | 2580 |
| agtttgagga | caagaagtct | gccctaaaaa | tagcgatgca | aaggcatggt gtccaagcca | 2640 |
| tacatatagc | gcactaattt | tatcagcaga | acaatggtat | ttataggtcc tagtgcccag | 2700 |
| gcaacaagag | acacgaataa | agcatcgatc | acgaca | | 2736 |

<210> SEQ ID NO 27
<211> LENGTH: 344
<212> TYPE: DNA
<213> ORGANISM: Zea mays

<400> SEQUENCE: 27

| | | | | |
|---|---|---|---|---|
| tgacaaagca | gcattagtcc | gttgatcggt | ggaagaccac | tcgtcagtgt tgagttgaat | 60 |
| gtttgatcaa | taaatacgg | caatgctgta | agggttgttt | tttatgccat tgataataca | 120 |
| ctgtactgtt | cagttgttga | actctatttc | ttagccatgc | caagtgcttt tcttattttg | 180 |
| aataacatta | cagcaaaaag | ttgaaagaca | aaaaaaaaa | cccccgaaca gagtgctttg | 240 |
| ggtcccaagc | tactttagac | tgtgttcggc | gttcccccta | aatttctccc cctatatctc | 300 |
| actcacttgt | cacatcagcg | ttctctttcc | cctatatctc | cacg | 344 |

<210> SEQ ID NO 28
<211> LENGTH: 711

<212> TYPE: DNA
<213> ORGANISM: Artificial Sequence
<220> FEATURE:
<223> OTHER INFORMATION: the open reading frame of mCherryW gene

<400> SEQUENCE: 28

| | | | | | |
|---|---|---|---|---|---|
| atggtgtcca | agggcgagga | ggacaacatg | gccatcatca | aggagttcat | gcgcttcaag | 60 |
| gtgcacatgg | agggctccgt | gaacggccac | gagttcgaga | tcgagggcga | gggcgagggc | 120 |
| cgcccctacg | agggcaccca | aaccgccaag | ctcaaggtga | ccaagggtgg | ccccctcccc | 180 |
| ttcgcctggg | acatcctctc | cccacaattc | atgtacggct | ccaaggccta | cgtgaagcac | 240 |
| cccgccgaca | tccccgacta | cctcaagctc | tccttccccg | agggcttcaa | gtgggagcgc | 300 |
| gtgatgaact | tcgaggacgg | cggcgtggtg | accgtgaccc | aagactcctc | cctccaagac | 360 |
| ggcgagttca | tctacaaggt | gaagctccgc | ggcaccaact | tcccctccga | cggccccgta | 420 |
| atgcaaaaga | gaccatgggc | ctgggaggcc | tcctccgagc | ggatgtaccc | cgaggacggc | 480 |
| gccctcaagg | gcgagatcaa | gcaaaggctc | aagctcaagg | acggcggcca | ctacgacgcc | 540 |
| gaggtgaaga | ccacctacaa | ggccaagaag | cccgtgcaac | tccccggcgc | ctacaacgtg | 600 |
| aacatcaagc | tcgacatcac | ctcccacaac | gaggactaca | ccatcgtgga | gcaatacgag | 660 |
| cgcgccgagg | gccgccactc | caccggcggc | atggacgagc | tgtacaagtg | a | 711 |

<210> SEQ ID NO 29
<211> LENGTH: 1149
<212> TYPE: DNA
<213> ORGANISM: Artificial Sequence
<220> FEATURE:
<223> OTHER INFORMATION: the CaMV35S enhancer-LTP2 promoter

<400> SEQUENCE: 29

| | | | | | |
|---|---|---|---|---|---|
| cgtcaacatg | gtggagcacg | acacgcttgt | ctactccaaa | aatatcaaag | atacagtctc | 60 |
| agaagaccaa | agggcaattg | agacttttca | acaaagggta | atatccggaa | acctcctcgg | 120 |
| attccattgc | ccagctatct | gtcactttat | tgtgaagata | gtggaaaagg | aaggtggctc | 180 |
| ctacaaatgc | catcattgcg | ataaaggaaa | ggccatcgtt | gaagatgcct | ctgccgacag | 240 |
| tggtcccaaa | gatggacccc | cacccacgag | gagcatcgtg | gaaaaagaag | acgttccaac | 300 |
| cacgtcttca | aagcaagtgg | attgatgtga | tgaattcaac | cgtctcttcg | tgagaataac | 360 |
| cgtggcctaa | aaataagccg | atgaggataa | ataaaatgtg | tggtacagt | acttcaagag | 420 |
| gtttactcat | caagaggatg | cttttccgat | gagctctagt | agtacatcgg | acctcacata | 480 |
| cctccattgt | ggtgaaatat | tttgtgctca | tttagtgatg | ggtaaatttt | gtttatgtca | 540 |
| ctctaggttt | tgacatttca | gttttgccac | tcttaggttt | tgacaaataa | tttccattcc | 600 |
| gcggcaaaag | caaacaatt | ttattttact | tttaccactc | ttagctttca | caatgtatca | 660 |
| caaatgccac | tctagaaatt | ctgtttatgc | cacagaatgt | gaaaaaaaac | actcacttat | 720 |
| ttgaagccaa | ggtgttcatg | gcatggaaat | gtgacataaa | gtaacgttcg | tgtataagaa | 780 |
| aaaattgtac | tcctcgtaac | aagagacgga | aacatcatga | acaatcgcg | tttggaaggc | 840 |
| tttgcatcac | ctttggatga | tgcgcatgaa | tggagtcgtc | tgcttgctag | ccttcgccta | 900 |
| ccgcccactg | agtccgggcg | gcaactacca | tcggcgaacg | acccagctga | cctctaccga | 960 |
| ccggacttga | atgcgctacc | ttcgtcagcg | acgatggccg | cgtacgctgg | cgacgtgccc | 1020 |
| ccgcatgcat | ggcggcacat | ggcgagctca | gaccgtgcgt | ggctggctac | aaatacgtac | 1080 |
| cccgtgagtg | ccctagctag | aaacttacac | ctgcaactgc | gagagcgagc | gtgtgagtgt | 1140 | agccgagta 1149

<210> SEQ ID NO 30
<211> LENGTH: 310
<212> TYPE: DNA
<213> ORGANISM: Solanum tuberosum

<400> SEQUENCE: 30

```
ctagacttgt ccatcttctg gattggccaa cttaattaat gtatgaaata aaaggatgca    60
cacatagtga catgctaatc actataatgt gggcatcaaa gttgtgtgtt atgtgtaatt   120
actagttatc tgaataaaag agaaagagat catccatatt tcttatccta aatgaatgtc   180
acgtgtcttt ataattcttt gatgaaccag atgcatttca ttaaccaaat ccatatacat   240
ataaatatta atcatatata attaatatca attgggttag caaaacaaat ctagtctagg   300
tgtgttttgc                                                          310
```

<210> SEQ ID NO 31
<211> LENGTH: 47
<212> TYPE: DNA
<213> ORGANISM: Triticum aestivum L.

<400> SEQUENCE: 31

```
cacagcatcc aggtgctggt ggaccagccc atggtcgggc agggcgt               47
```

<210> SEQ ID NO 32
<211> LENGTH: 42
<212> TYPE: DNA
<213> ORGANISM: Triticum aestivum L.

<400> SEQUENCE: 32

```
cacagcatcc aggtgctggt ggaccagggt cgggcagggc gt                    42
```

<210> SEQ ID NO 33
<211> LENGTH: 102
<212> TYPE: DNA
<213> ORGANISM: Triticum aestivum L.
<220> FEATURE:
<221> NAME/KEY: misc_feature
<222> LOCATION: (33)..(87)
<223> OTHER INFORMATION: a 55 bp insertion, and n is a, t, g or c.

<400> SEQUENCE: 33

```
cacagcatcc aggtgctggt ggaccagccc atnnnnnnnn nnnnnnnnnn nnnnnnnnnn    60
nnnnnnnnnn nnnnnnnnnn nnnnnnggt cgggcagggc gt                      102
```

<210> SEQ ID NO 34
<211> LENGTH: 88
<212> TYPE: DNA
<213> ORGANISM: Triticum aestivum L.
<220> FEATURE:
<221> NAME/KEY: misc_feature
<222> LOCATION: (31)..(84)
<223> OTHER INFORMATION: a 55 bp insertion, and n is a, t, g or c.

<400> SEQUENCE: 34

```
cacggcatcc aggtgctggt ggaccagccc nnnnnnnnnn nnnnnnnnnn nnnnnnnnnn    60
nnnnnnnnnn nnnnnnnnnn nnnngcgt                                      88
```

<210> SEQ ID NO 35
<211> LENGTH: 38
<212> TYPE: DNA
<213> ORGANISM: Triticum aestivum L.

```
<400> SEQUENCE: 35
cacagcatcc aggtgctggt ggaccagccg cagggcgt                              38

<210> SEQ ID NO 36
<211> LENGTH: 143
<212> TYPE: DNA
<213> ORGANISM: Triticum aestivum L.
<220> FEATURE:
<221> NAME/KEY: misc_feature
<222> LOCATION: (25)..(127)
<223> OTHER INFORMATION: a 55 bp insertion, and n is a, t, g or c.

<400> SEQUENCE: 36
cacggcatcc aggtgctggt ggacnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnntgg tcgggcaggg cgt                                            143
```

WHEAT FERTILITY-RELATED GENE TAMS7 AND APPLICATION METHOD THEREOF

TECHNICAL FIELD

The present application relates to the field of biotechnology, in particularly to a wheat hybrid breeding method, inducing the preparation of wheat nucleic sterile line and the production of hybrid seed, and more particularly to a wheat male nucleic sterile gene and a mutant thereof and use in hybrid breeding.

BACKGROUND

Wheat is a self-pollination crop, and the core of heterosis utilization thereof is to establish a technical system for efficiently producing wheat hybrid seeds. At present, there are three major routes of the heterosis utilization in wheat production: the first route is three-line system, namely the nucleo-cytoplasmic interaction male sterile line is used to produce hybrid seeds through the interaction of sterile lines, maintainer lines and restorer lines; the second route is utilization of chemically induced male sterility line, namely chemical hybridization agents are applied to induce male sterile line in wheat for hybrid seed production; and the third route is two-line system, namely the photo-thermo-sensitive sterile line, whose fertility is changed by photoperiod and temperature, is used for hybrid seed production. The three-line system has been researched since the 1950s, so far, more than 70 wheat nucleo-cytoplasmic interaction male sterile lines have been bred, and the most studied male sterile lines are T type, K type and Q type, whose cytoplasm thereof is mainly derived from various kinds of *Aegilops*, Triticumtimopheevii, wild oats, Haynaldiavillosa and the like. Although the three-line combinations for most of these sterile lines have been achieved, because of their own insurmountable genetic defects, such as fewer restorer sources, adverse effect of alien cytoplasm, low selection rate of strong superiority combinations, and low purity of sterile line seeds, these sterile lines have not been wildly used in production. In the 1980s, the research on chemical hybriding method reached a high tide. Because of overcoming various problems of the three-line system, the chemical hybriding method was once known as a promising new hybrid seed production technology. However, chemical hybridizing agents have many shortcomings, such as poor stability, residues of chemicals, toxic and side effects of chemicals, heavy environmental pollution and the like. A perfect chemical hybridization agent needs to be further developed so as to be wildly used in production. In the case that the three-line system and the chemical hybriding method are beset with many difficulties, the two-line system of hybrid wheat is rapidly developed and gradually becomes a principal development tendency of wheat heterosis research and utilization in future.

The core of two-line system is the photo-thermo-sensitive male sterile line, which is a kind of male sterile line caused by the interaction between genotype and environment. The photo-thermo-sensitive male sterile line has dual function (both male sterile line and maintainer line), which simplifies the reproductive procedure of sterile line, makes the seed production simpler, has a wider range of the restorer lines, makes breeding hybrids of superior heterosis easier, so two-line system has a very high value of popularization. At present, an original two-line hybrid wheat application technology system in China is ahead of the international level, the selected hybrid wheat varieties have strong stress resistance and high utilization rate of water and fertilizer, and their yield increase can reach 15%-20%, which has a significant effect on saving cost and increasing efficiency of the grain production. However, the male sterility of the photo-thermo-sensitive sterile line highly depends on environmental factors, and the variation of the environment seriously affects yield, quality and purity of the hybrid seeds, therefore, it may take some time that the two-line method hybrid wheat breaks through the production, and a key point is that the effect of the environment needs to be solved.

In the case that the above traditional conventional breeding modes encounter the bottleneck, a biological breeding technology which is dominated by modern molecular biology may be a key point for breaking through the bottleneck. The core of the wheat heterosis utilization is to establish the efficient technical system for producing the wheat hybrid seeds, while a key point of establishing the efficient wheat hybrid seed production technology is to acquire a suitable male sterile line as female parent. The male sterile means that the plant can not produce anthers, pollens or male gametes with normal functions in a sexual propagation process, and the mechanism of male sterile is the basis of improving wheat yield and quality using the heterosis.

The genome of wheat is huge and complicated, so little information from research has been accumulated on the mechanism of wheat male sterile until now. Therefore, the application of modem molecular biology and cell biology to the research of the mechanism of male sterile in wheat has important theoretical and practical significance for enhancing the research and utilization of wheat heterosis.

SUMMARY

All references mentioned in the application are incorporated into the application by reference.

Unless otherwise specified, all technical and scientific terms used in the application have the same meanings as that understood by those of ordinary skill in the art of the application. Unless otherwise specified, techniques used or mentioned in the application are standard techniques publicly known by those of ordinary skill in the art. Materials, methods and examples are only used for explaining, and are not intended to limit.

The application provides a fertility-related gene TaMS7, and a nucleotide sequence of the fertility-related gene is selected from one of the following groups of sequences:
   (a) a nucleotide sequence as shown in SEQ ID NO: 1, 2, 3, 4, 5 or 6;
   (b) a nucleotide sequence which encodes an amino acid sequence as shown in SEQ ID NO: 7, 8 or 9;
   (c) a DNA sequence capable of hybridizing with the DNA sequences in (a) or (b) under stringent conditions; or
   (d) a DNA sequence which has 80% (preferably at least 85%) similarity with any one of the sequences of (a)-(c) and has a fertility-related function; or
   (e) a DNA sequence complementary to any one of the sequences of (a)-(d).

It is to be noted by those skilled in the art that the fertility-related gene of the application further includes a homologous gene sequence which has a high homology with the nucleotide sequence or a protein sequence of the TaMS7 gene, and has the same fertility regulation or restoration function. The homologous gene with the high homology and the fertility regulation function includes a DNA sequence capable of hybridizing with the DNA sequence as shown in SEQ ID NO: 1, 2, 3, 4, 5 or 6 or a nucleotide sequence encoding an amino acid sequence which has 85% similarity or more with the amino acid sequence as shown in SEQ ID NO: 7, 8 or 9. The 'stringent conditions' used in the application are well known: for example, hybridizing for 12-16 hours at 53-60 DEG. C in a hybridization solution containing 400 mM NaCl, 40 mM PIPES (pH 6.4) and 1 mM EDTA, then washing with wash solution containing 0.5× SSC and 0.1% SDS for 15-60 minutes at 62-68 DEG. C.

The above homologous gene further includes a DNA sequence which has at least 80%, 85%, 90%, 95%, 98% or 99% similarity with full length sequence as shown in SEQ ID NO: 1, 2, 3, 4, 5 or 6 and also has the fertility regulation function, which may be isolated from any plant. A percentage of the sequence similarity may be obtained by a public biological informatics algorithm, including a Myers and Miller algorithm, a Needleman-Wunsch global alignment method, a Smith-Waterman local alignment method, a Pearson and Lipman similarity search method, and a Karlin and Altschul algorithm. It is well known to those skilled in the art.

The application further provides an expression cassette, the expression cassette contains the DNA sequence of the fertility-related gene disclosed by the application, and the nucleotide sequence of the fertility-related gene is selected from one of the following groups of sequences:
   (a) a nucleotide sequence as shown in SEQ ID NO: 1, 2, 3, 4, 5 or 6;
   (b) a nucleotide sequence which encodes an amino acid sequence as shown in SEQ ID NO: 7, 8 or 9;
   (c) a DNA sequence capable of hybridizing with the DNA sequences in (a) or (b) under stringent conditions; or
   (d) a DNA sequence which has 80% (preferably at least 85%) similarity with anyone of the sequences of (a)-(c) and has a fertility restoration function; or
   (e) a DNA sequence complementary to any one of the sequences of (a)-(d).

Specifically, the fertility-related gene in the above expression cassette is further operably connected with a promoter which can drive the expression of the fertility-related gene, the promoter includes, but not limit to, a constitutive expression promoter, an inducible promoter, a tissue-specific promoter, or a spatiotemporal-specific promoter More specifically, the promoter is an anther-specific promoter. Preferably, a nucleotide sequence of the anther-specific promoter is shown in SEQ ID NO: 16.17 or 18.

The above expression cassette of the application further includes a pollen inactivation gene, the pollen inactivation gene can disturb the function or formation of male gametes containing the pollen inactivation gene in a plant. The pollen inactivation gene includes, but not limited to, a barnase gene, an amylase gene, a DAM methylase and the like. More specifically, the pollen inactivation gene is a maize α-amylase gene, preferably a nucleotide sequence of the pollen inactivation gene is shown as SEQ ID NO: 25.

The above expression cassette of the application further includes a screening gene, the screening gene can be used for screening a plant, a plant tissue cell or a vector containing the expression cassette. The screening gene includes, but not limited to, an antibiotics resistant gene, or a herbicide-resistant gene, or a fluorescent protein gene and the like Specifically, the screening gene includes, but not limited to, a chloramphenicol-resistant gene, a hygromycin resistant gene, a streptomycin resistant gene, a miramycin resistant gene, a sulfonamide resistant gene, a glyphosate resistant gene, phosphinothricin resistant gene, a bar gene, a red fluorescence gene DsRED, a mCherry gene, a cyan fluorescence protein gene, a yellow fluorescence protein gene, a luciferase gene, a green fluorescence protein gene and the like.

The application further discloses a method for regulating plant fertility, the method means transforming an ms7 male sterile mutant with the fertility-related gene to restore the male fertility of the ms7 male sterile mutant, herein the nucleotide sequence of the fertility-related gene is selected from one of the following groups of sequences:
   (a) a nucleotide sequence as shown in SEQ ID NO: 1, 2, 3, 4, 5 or 6.
   (b) a nucleotide sequence which encodes an amino acid sequence as shown in SEQ ID NO: 7, 8 or 9;
   (c) a DNA sequence capable of hybridizing with the DNA sequences in (a) or (b) under stringent conditions, or
   (d) a DNA sequence which has 80% (preferably at least 85%) similarity with any one of the sequences of (a)-(c) and has a fertility restoration function; or
   (e) a DNA sequence complementary to any one of the sequences of (a)-(d).

The application further provides a method for regulating plant fertility by affecting the expression of the fertility gene TaMS7. An ms7 male sterile mutant material is obtained through, but not limited to, a method of mutating TaMS7 gene; or the TaMS7 gene is used for restoring the male sterile phenotype caused by the mutation of TaMS7 through gene complementation, and restoring sterility of ms7male sterile mutant to fertility. In the application, the mutation includes substitution, deletion or insertion of one or more nucleotides in a nucleotide sequence of a fertility regulating gene. Methods of gene mutation include, but not limited to, physical mutagenesis, chemical mutagenesis, RNAi or gene editing such as TALEN, CRISPR-Cas9 and the like.

The application further includes a method for preparing the ms7 male sterile mutant, the method is a process that contains mutating endogenous fertility-regulating gene TaMS7 or the nucleotide sequence of its highly homologous gene to obtain the male sterile plant. The amino acid sequence of fertility regulating gene TaMS7 mentioned above is shown as SEQ ID NO: 7, 8 or 9 The nucleotide sequence of fertility regulating gene TaMS7 is shown as SEQ ID NO: 1, 2, 3, 4, 5 or 6. The 'mutation' includes, but not limited to, gene mutation caused by the following methods, such as a physical or chemical method, the chemical method includes mutagenesis caused by mutagen such as EMS etc, the mutation may also be point mutation, or DNA deletion or insertion, or gene silencing by means of RNAi, site-directed mutagenesis and so on, the gene site-directed mutagenesis includes, but not limited to, ZFN, TALEN, and/or CRISPR/Cas9 gene editing methods and the like.

The application further provides a method for using ms7 mutant, herein the mutant is caused by the mutation of the nucleotide sequence, the plant containing the mutated nucleotide sequence showed male sterile phenotype, herein the nucleotide sequence is the nucleotide sequence of the TaMS7 gene, preferably shown as SEQ ID NO: 1, 2, 3, 4, 5 or 6. The use of the male sterile mutant includes, but not limited to, an use in hybrid breeding, more specifically, it is that the ms7mutant plant is used as male sterile female parent, and hybridized with the restorer line to produce the hybrid seeds.

The application further discloses a method of maintaining the male sterile line. The method comprises using the ms7 male sterile mutant as an acceptor material of transformation, and transforming the acceptor plant with 3 closely-linked target genes. The 3 target genes are the fertility-related gene TaMS7, a pollen inactivation gene and a selection marker gene respectively. Herein, the fertility-related gene TaMS7 can restore the fertility of the sterile acceptor of transformation, the pollen inactivation gene may inactivate the pollen containing the transformed exogenous gene, namely fertilization ability is lost, the screening gene may be used for sorting transgenic seeds or tissues and non-transgenic seeds or tissues, the sorted non-transgenic seeds are used as the sterile line for producing the hybrid seeds, and the transgenic seeds are used as the maintainer line for producing the sterile line continuously and stably.

In the application, the wheat ms7 male sterile mutant is the male sterile mutant caused by the mutation of TaMS7 gene. The ms7 male sterile mutant in the application may also be called as the ms7 sterile line or the ms7male sterile line.

In the above method for maintaining male sterile line, the pollen inactivation gene includes, but not limited to, a barnase gene, an amylase gene, a DAM methylase and the like. More specifically, the pollen inactivation gene is a maize α-amylase gene Zm-AA, preferably a nucleotide sequence thereof is shown as SEQ ID NO: 25. The pollen inactivation gene is connected with a male gamete-specific promoter. More specially, the male gamete-specific promoter includes: but not limited to, a PG47 promoter, a Zm13 promoter and the like. The screening gene may be used for selecting out the plants or the vectors containing the expression cassette. The screening gene includes, but not limited to: an antibiotics resistant gene, or a herbicide-resistant gene, or a fluorescent protein gene and the like. Specifically, the screening gene includes but not limited to: a chloramphenicol-resistant gene, a hygromycin resistant gene, a streptomycin resistant gene, a miramycin resistant gene, a sulfonamide resistant gene, a glyphosate resistant gene, phosphinothricin resistant gene, a bar gene, a red fluorescence gene DsRED, a mCherry gene, a cyan fluorescence protein gene, a yellow fluorescence protein gene, a luciferase gene, a green fluorescence protein gene and the like.

The application further discloses a method for propagating the male sterile line, the method includes the following steps:
  (a) transforming the ms7 male sterile line with the following vector to obtain the maintainer line containing the following vector: a fertility-related gene TaMS7, which can restore the male fertility of the ms7 male sterile line; and a pollen inactivation gene, the expression of which disturbs the function or formation of male gametes containing the pollen inactivation gene in a plant, so the fertile male gametes generated in the plant do not contain the vector; and a screening gene, which is used for sorting transgenic seeds or a tissues and non-transgenic seeds or a tissues; and
  (b) selfing the maintainer line plants transformed with the above vector to produce ms7 male sterile line seeds without the vector and maintainer line seeds containing the vector; or pollinating ms7 male sterile line plants with the pollen grains of the maintainer line plants to propagate the seeds of the ms7 male sterile line.

In the above method for propagating the male sterile line, the pollen inactivation gene includes, but not limited to, a barnase gene, an amylase gene, a DAM methylase and the like. More specifically, the pollen inactivation gene is a maizeα-amylase gene Zm-AA, preferably a nucleotide sequence of the pollen inactivation gene is shown as SEQ ID NO: 25 The pollen inactivation gene is connected with a male gamete-specific promoter. More specifically, the promoter with gamete expression specificity includes, but not limited to, a PG47 promoter, a Zm13 promoter and the like.

The screening gene can be used for selecting plants or vectors containing the expression cassette. The screening gene includes, but not limited to, an antibiotics resistant gene, or a herbicide-resistant gene, or a fluorescent protein gene and the like. Specifically, the screening gene includes, but not limited to, a chloramphenicol-resistant gene, a hygromycin resistant gene, a streptomycin resistant gene, a miramycin resistant gene, a sulfonamide resistant gene, a glyphosate resistant gene, phosphinothricin resistant gene, a bar gene, a red fluorescence gene DsRED, a mCherry gene, a cyan fluorescence protein gene, a yellow fluorescence protein gene, a luciferase gene, a green fluorescence protein gene and the like.

The application further discloses a method for producing a maintainer line, the method includes the following steps:
  (a) transforming the ms7 male sterile line with the following vector, to obtain the maintainer line containing the following vector a fertility-related gene TaMS7, which can restore the male fertility of the ms7 male sterile line; and a pollen inactivation gene, the expression of which disturbs a function or formation of male gametes containing the pollen inactivation gene in a plant, so the fertile male gametes generated in the plant do not contain the vector; and a screening gene, which is used for sorting transgenic seeds and non-transgenic seeds.
  (b) selfing the maintainer line plants transformed with the above vector to produce ms7 male sterile line seeds without the vector and maintainer line seeds containing the vector, or pollinating ms7 male sterile line plants with the pollen grains of the maintainer line plants to propagate the seeds of the ms7 male sterile line.

In the above method for producing the maintainer line, the pollen inactivation gene includes, but not limited to, a barnase gene, an amylase gene, a DAM methylase and the like. More specifically, the pollen inactivation gene is a maize α-amylase gene Zm-AA, preferably a nucleotide sequence of the pollen inactivation gene is shown as SEQ ID NO: 25. The pollen inactivation gene is connected with a male gamete-specific promoter. More specifically, the male gamete-specific promoter includes, but not limited to, a PG47 promoter, a Zm13 promoter and the like. The screening gene can be used for screening plants or vectors containing the expression cassette. The screening gene includes, but not limited to, an antibiotics resistant gene, or a herbicide-resistant gene, or a fluorescent protein gene and the like. Specifically, the screening gene includes, but not limited to, a chloramphenicol-resistant gene, a hygromycin resistant gene, a streptomycin resistant gene, a miramycin resistant gene, a sulfonamide resistant gene, a glyphosate resistant gene, phosphinothricin resistant gene, a bar gene, a red fluorescence gene DsRED, a mCherry gene, a cyan fluorescence protein gene, a yellow fluorescence protein gene, a luciferase gene, a green fluorescence protein gene and the like.

The application further discloses a method for propagating the maintainer line, the method includes the following steps:
  (a) transforming the ms7 male sterile line with the following vector to obtain the maintainer line containing the following vector: a fertility-related gene TaMS7, which can restore the male fertility of the ms7 male sterile line; and a pollen inactivation gene, the expression of which disturbs the function or formation of male gametes containing the pollen inactivation gene in a plant, so the fertile male gametes generated in the plant do not contain the vector; and a screening gene, which is used for sorting transgenic seeds and non-transgenic seeds; and (b) selling maintainer line plants transformed with the above vector to produce ms7 male sterile line seeds without the vector and maintainer line seeds containing the vector in the proportion of 1:1.

The application further discloses a method for producing seeds, the method includes the following steps:

(a) transforming the ms7 male sterile line with the following vector to obtain the maintainer line containing the following vector a fertility-related gene TaMS7 which can restore the male fertility of the ms7 male sterile line; and a pollen inactivation gene, the expression of which disturbs the function or formation of a male gamete containing the pollen inactivation gene in a plant, so the fertile male gametes generated in the plant do not contain the vector;

(b) selling a maintainer line plant obtained by transforming with the above vector; and (c) after the selling, ms7 male sterile line seeds without the vector and maintainer line seeds containing the vector are obtained.

In the above method for propagation or maintaining the male sterile line, the method for producing or the propagating the maintainer line, and the method for producing seeds and the like of the application, step (a) may also be: introducing the vector containing the fertility-related gene TaMS7, the pollen inactivation gene and the screening gene to a common plant, after obtaining transgenic plants containing the vector, hybridizing the transgenic plant with the ms7 male sterile line, and through directed breeding, maintainer line plants containing the vector in the background of the ms7 male sterile line are obtained.

In the above method for propagating or maintaining the male sterile line, the method for producing or propagating the maintainer line, and the method for producing the seeds and the like of the application, the nucleotide sequence of the fertility-related gene is selected from one of the following groups of sequences:

(a) a nucleotide sequence as shown in SEQ ID NO: 1, 2, 3, 4, 5 or 6;

(b) a nucleotide sequence which encodes an amino acid sequence as shown in SEQ ID NO: 7, 8 or 9;

(c) a DNA sequence capable of hybridizing with the DNA sequences in (a) or (b) under stringent conditions; or (d) a DNA sequence which has 80% (preferably at least 85%) similarity with any one of the sequences of (a)-(c) and has a fertility restoration function; or (e) a DNA sequence complementary to any one of the sequences of (a)-(d).

The above fertility-related gene TaMS7 may be further operably connected with an anther-specific promoter, which drives the TaMS7 gene to express in the plant anthers. The promoter with anther expression specificity is selected from one of groups consisting of promoters of genes regulating fertility NP1、MSP1、、PAIR1、PAIR2、ZEP1、MELL、PSS1、TDR、UDT1、GAMYB4、PTC1、API5、WDA1、CYP704B2、MS26、MS22、DPW、MADS3、OSC6、RIP1、CSA、AID1、5126、Ms45 and the like. More specifically, the nucleotide sequence of the anther-specific promoter is shown as SEQ ID NO: 16, 17 or 18. The above fertility-related gene TaMS7 may also be operably connected with a terminator, which is a terminator of any gene disclosed publicly, specifically, the nucleotide sequence of the terminator is shown as SEQ ID NO: 22, 23 or 24.

In the above method for propagating or maintaining the male sterile line, the method for producing or propagating the maintainer line, and the method for producing the seeds and the like of the application, the pollen inactivation gene includes, but not limited to, a barnase gene, an amylase gene, a DAM methylase and the like. More specifically, the pollen inactivation gene is a maize α-amylase gene Zm-AA, preferably a nucleotide sequence of the pollen inactivation gene is shown as SEQ ID NO: 25. The pollen inactivation gene is connected with a male gamete-specific promoter More specifically, the male gamete-specific promoter includes, but not limited to, a PG47 promoter, a Zm13 promoter and the like.

In the above method for propagating or maintaining the male sterile line, the method for producing or propagating the maintainer line, and the method for producing the seeds and the like of the application, the screening gene is used for screening plants or vectors containing the expression cassette. The screening gene includes, but not limited to, an antibiotics resistant gene, or a herbicide-resistant gene, or a fluorescent protein gene and the like. Specifically, the screening gene includes, but not limited to, a chloramphenicol-resistant gene, a hygromycin resistant gene, a streptomycin resistant gene, a miramycin resistant gene, a sulfonamide resistant gene, a glyphosate resistant gene, phosphinothricin resistant gene, a bar gene, a red fluorescence gene DsRED, a mCherry gene, a cyan fluorescence protein gene, a yellow fluorescence protein gene, a luciferase gene, a green fluorescence protein gene and the like.

The application further provides an anther-specific promoter, the nucleotide sequence of the promoter is shown as SEQ ID NO: 16, 17 or 18. The SEQ ID NO: 16, 17 or 18 is inserted into a vector and connected with a reporter gene GUS. The rice and wheat are transformed with the vector, and the activity and expression pattern of GUS are detected and analyzed in transgenic plants. Through GUS staining analysis on roots, stems, leaves and flowers of the transgenic plant, it is discovered that the promoter provided by the application drives the expression of GUS gene in the anther of plant. It shows that the SEQ ID NO: 16, 17 or 18 provided by the application is an anther-specific promoter.

The anther-specific promoter provided by the application contains the nucleotide sequence of SEQ ID NO: 16, 17 or 18 in the sequence list, or contains the nucleotide sequence which has 90% similarity with the nucleotide sequence of SEQ ID NO: 16, 17 or 18, or contains a fragment with 500 and more than 500 continuous nucleotide derived from the SEQ ID NO: 16, 17 or 18 sequence, and the nucleotide sequence operably connected with the promoter is driven to express in the anther of plant. The expression vector containing the above sequence, the transgenic cell line and host bacteria and the like fall within the protection scope of the application. A primer pair for amplifying any one nucleotide fragment of the SEQ ID NO: 16, 17 or 18 promoters disclosed by the application falls within the protection scope of the application.

The term "promoter" used herein means a regulatory DNA region, commonly including TATA box which can guide RNA polymerase II to initiate RNA synthesis at a proper transcriptional initiation site of a specific coding sequence. The promoter may also include other recognition sequences commonly located in the upstream of the TATA box, named as an upstream promoter element with a function of regulating transcriptional efficiency. As known to those skilled in the art, although the nucleotide sequence of the promoter region has been identified in the application, the isolation and identification of other regulatory element located in upstream region of the TATA box of the specific promoter region disclosed in the application also falls in the scope of the application. Therefore, the promoter region disclosed in the application is generally further defined as sequences including the upstream regulatory elements or enhancer that regulates spatial and temporal expression patterns of the coding sequence. The promoter elements showing tissue-specific expression (for example, male tissue-specific) may be identified and isolated in the same way, and may be used together with other core promoter to examine the preferential expression in male-specific tissues. The core promoter means a minimal sequence required for transcriptional initiation, for example, the sequence known as the TATA box, which commonly exists in the promoter of protein-coding gene. Therefore, alternatively, the upstream promoter of TaMS7 gene may be used in association with its own core promoter or the core promoter from other sources.

The core promoter may be any known core promoters, such as 35S or 19S promoter of Cauliflower Mosaic Virus (U.S. Pat. No. 5,352,605), a Ubiquitin promoter (U.S. Pat. No. 5,510,474), a IN2 core promoter (U.S. Pat. No. 5,364,780), or a figwort mosaic virus promoter.

The function of the gene promoter may be analyzed by the following methods: the nucleotide sequence of the promoter is operably linked to reporter gene to form a vector which can be used in transformation, then the plants is transformed with the vector and the transgenic plants are obtained, and the expression of reporter gene in each tissue organ of the transgenic offspring plants is observed to determine the expression specificity. Alternatively, the promoter sequence linked to a reporter gene is subcloned into an expression vector for a transient expression experiment, and the function of the promoter or other regulatory regions thereof is detected through the transient expression experiment.

The selection of suitable expression vectors for testing the function of the promoter or regulatory regions thereof depends on the host and the method of introducing the expression vector into the host, and the method is well known to those of ordinary skill in the art. For eukaryotes, the sequence in the expression vector comprises regions controlling transcription initiation and controlling the processing. These regions are operably linked to a reporter gene including YFP, UidA, GUS gene or luciferase. The expression vector with a putative regulatory region located in the genome may be introduced into a whole organ, such as pollen at specific developmental stages, or callus for functional verification.

Furthermore, the promoter disclosed in the application may also be linked to nudeotide sequences other than the TaMS7 gene to drive their expression. The nucleotide sequence, fragment and variant of the promoter disclosed in the application can be assembled into an expression cassette with the heterogenous nucleotide sequence, and used for expression in target plants, more particularly, expression in male organs of the plant. The expression cassette has a proper restriction enzyme cleavage sites, which are used for insertion of the promoter and the heterogenous nucleotide sequence. The expression cassettes may be used for manipulation on any plant to obtain an expected corresponding phenotype.

The anther-specific promoter disclosed by the application may be used to drive the expression of the following heterologous nucleotide sequence to obtain the male sterile transgenic plants, the heterologous nucleotide sequence may encode an enzyme promoting the degradation of carbohydrate, or a modification enzyme, an amylase, a debranching enzyme, and a pectinase, more specifically, for example, a barnase gene, a maize α-amylase gene, an auxin gene, a rot 8 gene, a cytotoxin gene, diphtheria toxin gene. DAM methylase gene, or a dominant male sterility gene. In some embodiments, the nucleic acid which can be operably linked to the downstream of the promoter disclosed in the application may be a structural gene, a regulatory gene, an antisense sequence of the structural gene, an antisense sequence of the regulator gene or the gene of small RNA capable of interfering with the expression of a particular endogenous gene.

The application further provides a transcription terminator sequence, a nucleotide sequence of the transcription terminator is shown as SEQ ID NO 22, 23 or 24, and has a function of terminating the gene transcription.

The application further provides an expression cassette, a vector or an engineering strain, which contains the anther-specific promoter SEQ ID NO: 16, 17 or 18 provided by the application. Specifically, the nucleotide sequence of the fertility-related gene TaMS7 provided by the application may be constructed at the downstream of the promoter SEQ ID NO: 16, 17 or 18 provided by the application to drive the expression of the fertility gene in the acceptor plant of transformation.

The anther-specific promoter provided in the present disclosure may be used for the specific expression of an exogenous gene in anther to avoid the negative effect caused by the continuous expression of the exogenous gene in other tissues of the plant. The anther-specific promoter may also be used for the functional analysis and identification of genes related to the plant pollen development, may also be used for the construction of the male sterile line and the maintainer line, and may also be applied to a pollen abortion experiment to avoid the bio-safety problem caused by the flow of transgenic plants or pollen escape, and the anther-specific promoter has an important significance to the creation of the plant male sterile line and the maintainer line.

The nucleotide sequence and the promoter sequence or the expression cassette of the TaMS7 gene provided by the application may be inserted into a vector, a plasmid, a yeast artificial chromosome, a bacteria artificial chromosome or any other vectors suitable for transformation into a host cell Preferably the host cell is a bacteria cell, especially the cell for cloning or storing polynucleotide, or transforming a plant cell, such as *Escherichia coli, Agrobaterium tumefaciens* and *Agrobacterium rhizogenes*. In the case that the host cell is a plant cell, the expression cassette or the vector may be inserted into the genome of the transformed plant cell, and the insertion may be either site-specific or random.

The methods of introducing the nudeotide sequence, the vector or the expression cassette into the plant, or transforming the plant with them in the application are conventional transgenic methods through which the nucleotide sequence, the vector or the expression cassette is transformed into the acceptor cell or the acceptor plant Any transgenic methods known by those skilled in the plant biotechnology art may be used for introducing a recombinant expression vector into the plant cell, so the transgenic plant of the application is produced. The transformation methods include direct and indirect transformation methods. The proper direct transformation methods include DNA intake induced by polyethylene glycol, lipidosome-mediated transformation, particle bombardment, electroporation and micro-injection. The transformation methods also include an *Agrobacterium*-mediated plant transformation method and the like. Compared with the prior art, the application has the following benefits: the application provides a fertility-related gene TaMS7 and a promoter thereof, and methods in which TaMS7 gene is used for propagation and maintenance of an ms7 male sterile line. The fertility-related gene and the method have important values of production, popularization and application in the hybrid breeding production of crops. The fertility gene provided by the application and the sterile line generated by the gene mutation provide resources for the wheat hybrid breeding, and also provide a necessary elements for constructing the third-generation hybrid breeding system. The male sterile line generated by the gene mutation is used for producing the hybrid seeds, which has an important significance to break through and improve the existing "three-line" and "two-line" hybrid breeding technology.

BRIEF DESCRIPTION OF THE DRAWINGS

FIG. 1 is expression analysis of comp155942_c0_seq4 in anthers while pollens are at meiosis stage (WT-0), mononuclear stage (WT-1), binuclear stage (WT-2) and trinuclear stage (WT-3). The horizontal coordinate indicates different pollen development stages, and the vertical coordinate indicates FPKM which reflects the expression level of the gene.

FIG. 2 is RT-PCR analysis of 3 homologous genes of TaMS7 in different tissue organs and anthers at different development stages of wheat; 1 represents roots, 2, represents stems, 3 represents leaves, 4 represents spikes with pollens at meiosis stage, 5 represents anthers with mononuclear microspores, 6 represents anthers with binuclear pollens, 7 represents anthers with trinuclear pollens, 8 represents flower organs except anthers with mononuclear microspores, 9 represents flower organs except anthers with binuclear pollens, and 10 represents flower organs except anthers with trinuclear pollens.

FIG. 3 shows genotypes and phenotypes of seven wheat recessive nucleic male sterile mutant strains obtained by CRISPR-Cas9 technology: the mutations were identified at the target sites (SEQ ID NO: 31) of the TaMS7-A, TaMS7-B, and TaMS7-D genes:a1 (SEQ ID NO: 32) and a2 (SEQ ID NO 33) represent two mutant genotypes of TaMS7-A respectively, b1 (SEQ ID NO: 34) represents one mutant genotype of TaMS7-B, d1 (SEQ ID NO: 35) and d2 (SEQ ID NO: 36) represent two mutant genotypes of TaMS7-D respectively.

DETAILED DESCRIPTION OF THE EMBODIMENTS

Figure 4:
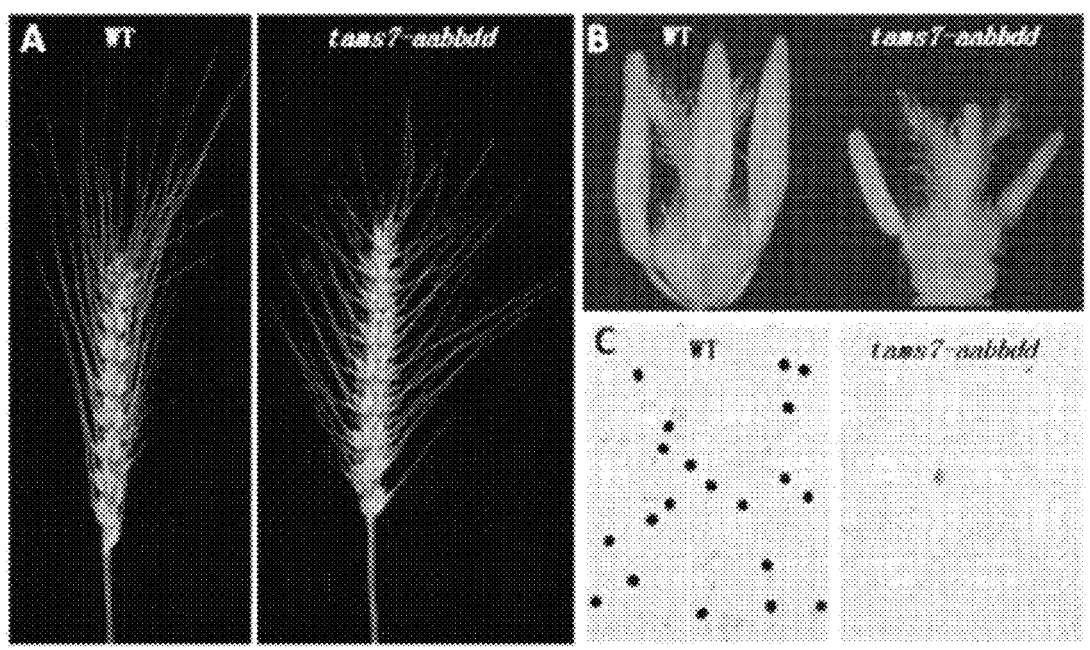
FIG. 4 The tams7triple mutant shows complete male sterile characters: A, Spikes of wild type and tams7 triple mutant; B, anthers and pistils of the wild type and tams7 triple mutant plant; C, Mature pollen grains of wild type and tams7 triple mutant stained with $I_2$-KI.

The embodiments of the application are described below in detail, the embodiments are implemented with the technical scheme of the invention as a precondition, and detailed implementation and specific operation process are provided, but the scope of protection of the invention is not limited to the following embodiments.

Embodiment 1. Analysis of Genome-Wide Expression Profiles of Wheat Anthers at Different Development Stages and Acquisition of Contigs Expressed in Anthers with Pollens at Early Development Stage Meiosis anthers and the anthers which have mononuclear microspore, binuclear pollens or trinuclear pollens were collected respectively Total RNA was extracted with Trizol (Invitrogen), and DNaseI (Promega) treatment was performed, thereby mRNA was purified (Ambion). Reverse transcription (Invitrogen) of purified mRNA, sonication (Fisher), library preparation (illumina) and amplification (illumina) and sequencing on illumine machine were performed successively.

The reads from high-throughput transcriptome sequencing were assembled with Trinity software, redundant sequences in assembled sequences were removed and similarity clustering analysis was performed. For expression change analysis of the assembled transcript contigs, the reads from high-throughput sequencing of each sample was firstly aligned with the assembled transcript contigs with TopHat (http://tophat.cbcb.umd.edu/) software. After that, the normalized expression values of transcripts contigs which can be aligned were measured with Cufflink software, and were represented as FPKM (fragments per kilobase of exon model per million mapped fragments).

By analyzing the genome-wide expression profiles of the wheat anthers at different development stages, we found that 7231 transcripts contigs were highly expressed in the anthers with pollens at meiosis stage and the mononuclear stage and not expressed in the anthers with pollens at binuclear stage and trinuclear stage. As shown in FIG. 1, the comp155942_c0 seq4 is highly expressed in the anthers with pollens at meiosis stage and the mononuclear stage and not expressed in the anthers with pollens at binuclear stage and trinuclear stage. The gene corresponding to the comp155942_c0_seq4 is named as TaMS7.

Embodiment 2. The Expression Specificity of TaMS7 Gene in Different Tissues was Verified by RT-PCR Because wheat is an allohexaploid composed of three sets of genomes A, B and D, an average copy number of genes is 2.8, nearly half of which (46%) have 3-4 copies, 12% of which have 1-2 copies, and 42% of which have 5 or more than 5 copies. Using the sequence of comp155942_c0_seq4, sequencing information of common wheat published by CerealsDB and IWGSC (International Wheat Genome Sequencing Consortium), and sequencing information of *Triticum Urartu* (A genome donor) and *Aegilops tauschii* (D genome donor) published on Nature in 2013, we obtained 3 TaMS7 genes which were named as TaMS7-A. TaMS7-B and TaMS7-D respectively.

The genomic DNA sequences of three TaMS7genes were shown in SEQ ID NO: 1, SEQ ID NO: 2 and SEQ ID NO: 3 respectively, the identity of which is 95%-97%; CDS sequences were shown in SEQ ID NO: 4, SEQ ID NO: 5 and SEQ ID NO: 6 respectively, the identity of which is 97%-98%; and protein sequences were shown in SEQ ID NO: 7, SEQ ID NO: 8 and SEQ ID NO: 9 respectively, the identity of which is 98%-99%.

Specific primers of TaMS7-A, TaMS7-B and TaMS7-D CDS were designed respectively, and the expression specificity of the three genes in multiple tissue of wheat (roots, stems and leaves, anthers at different development stages and other floral organs except the anthers and the like) were analyzed by RT-PCR, the result, as shown in FIG. 2, revealed that the TaMS7 genes were only specifically expressed in spikes with pollens at meiosis stage and anthers with pollens at mononuclear stage, not expressed in the anthers with pollens at binuclear stage and trinuclear stage, and not expressed in other floral organs except the anthers at different developmental stage and roots, stems and leaves.

This result indicated that the TaMS7 genes were genes specifically expressed in the anthers, and only specifically expressed in the anthers with pollens at early developmental stage, and the promoters of TaMS7 genes were anther-specific promoters.

```
The primers of the TaMS7-A gene for RT-PCR are
as follows:
                                    (SEQ ID NO: 10)
Primer 1:   5'-ATACTGACACAAGTTTATGGGGCTG-3'

(SEQ ID NO: 11)
Primer 2:   5'-AATTACATTCAAATATGGCTCCTTG-3'

The primers of the TaMS7-B gene for RT-PCR are
as follows:
                                    (SEQ ID NO: 12)
Primer 3:   5'-GGCCTCGTGAACTCGTCGTATC-3'

(SEQ ID NO: 13)
Primer 4:   5'-TGAATTACATGCAAATTTGGCTCCG-3'

The primers of the TaMS7-D gene for RT-PCR are
as follows:
                                    (SEQ ID NO: 14)
Primer 5:   5'-ATGTCCAACCAGGAGCACTTCAC-3'

(SEQ ID NO: 15)
Primer 6:   5'-GCACAGTTTTTTGAAGCAATGTTG-3'
```

Embodiment 3. Acquisition of Promoter Sequence of TaMS7 Gene

Using the genomic DNA sequences of TaMS7-A, TaMS7-B and TaMS7-D gene, sequencing information of common wheat published by CerealsDB and IWGSC (International Wheat Genome Sequencing Consortium), and sequencing information of *Triticum Urartu* (A genome donor) and *Aegilops tauschii* (D genome donor) published on Nature in 2013, we isolated the promoters of the TaMS7-A, TaMS7-B and TaMS7-D gene, which were named as TaMS7-A promoter, TaMS7-B promoter and TaMS7-ID promoter respectively, and also called as pTaMS7-A, pTaMS7-B and pTaMS7-D respectively in this application. The lengths of the promoters thereof were 2601 bp, 2635 bp and 2821 bp respectively, and the nucleotide sequences thereof were shown in SEQ ID NO 16, SEQ ID NO: 17 and SEQ ID NO: 18 respectively.

Embodiment 4 Cloning of TaMS7-D Promoter and Construction of Plant Expression Vector In order to further verify functions of the above promoter, we performed a function verification experiment of TaMS7-D promoter in this application. The plant expression vector pBI121 was double-digested by restriction enzyme HindIII and EcoRI, the obtained 35S:GUS fragment was ligated with T4DNA ligase into the pCAMBIA2300 vector of the CAMBIA corporation which was also double-digested by HindIII and EcoRI, and the new vector was named as p2300 35S GUS.

Primers were designed at the 5'-terminal of TaMS7-D promoter and the upstream of ATG:

```
Primer 7:
                                    (SEQ ID NO: 19)
5'-aagcttCTGACATAGTACATGTAATCTTTAAATCCATAAC-3'

Primer 8:
                                    (SEQ ID NO: 20)
5'-ggatccTTGCGCCGGCGAGCTCGGC-3'
```

The sequence aagctt in Primer 7 is the restriction site of HindIII, and the sequence ggatcc in Primer 8 is the restriction site of BamHI.

The genomic DNA of wheat was used as a template, Primer 7 and Primer 8 were used for amplification, reaction conditions were as follows: initial denaturation at 94 DEG. C for 5 minutes; followed by thirty-five cycles, including denaturation at 94 DEG. C for 30 seconds; annealing at 60 DEG. C for 30 seconds; elongation at 72 DEG. C for two minutes and 30 seconds; and final elongation at 72 DEG. C for 10 minutes. After the reaction, the PCR product was detected and recovered by 1% of agarose gel electrophoresis. The recovered product was inserted into the pMD20-T vector, positive clone was screened and sequenced, and the sequence was shown in SEQ ID NO: 18. The plasmid was called as T-pTaMS7-D.

The T-pTaMS7-D was double-digested by restriction enzyme HindIII and BamHI, the obtained TaMS7-D promoter was ligated with T4 DNA ligase into the p2300 35S:GUS vector which was also double-digested by HindIII and BamHI, then a plant expression vector p2300pTaMS7-D:GUS was obtained.

Embodiment 5. Genetic Transformation of Rice and Histochemistry Detection of GUS Gene Expression in Different Tissue Organs of Transgenic Rice Plant The plant expression vector p2300pTaMS7-D:GUS was transformed into *Agrobacterium tumefaciens* AGL0 strains by a heat shock method.

The *Agrobacterium tumefaciens* was used to infect rice embryonic callus, then the *Agrobacterium tumefaciens* and the rice embryonic calli were co-cultured in the dark for 2-3 days. After two steps of resistance screening, pre-differentiating, differentiating, rooting and the like, the transgenic rice $T_0$-generation plants of p2300pTaMS7-D:GUS with kanamycin resistance were obtained finally.

Transgenic seedlings of suitable size or specific tissues were selected to be immerged in GUS staining buffer, and were incubated overnight at 37 DEG. C. Then, the reaction solution was removed, gradient decoloration was performed by ethyl alcohol, and a microscope was used for observation. The results showed that the expression of GUS gene was not detected in nutritive organs of transgenic rice such as roots, stems and leaves and the like, and the expression of GUS gene was not detected in anthers and other floral organs with binuclear and trinuclear pollens, and other floral organs except the anthers with pollens at meiosis stage and mononuclear stage, the TaMS7-D promoter only drived GUS gene to express in the anthers with pollens at meiosis stage and mononuclear stage, so it is indicated that the TaMS7-D promoter is a anther-specific promoter at early stage of pollen development. According to a function verification process of the TaMS7-D promoter, the function of TaMS7-A promoter and TaMS7-B promoter was also verified, it was discovered that the TaMS7-A promoter and the TaMS7-B promoter were the anther-specific promoters too, which was consistent with the experiment results in the embodiment 2.

Embodiment 6. Site-Directed Knockout of TaMS7 Fertility Gene and Phenotype Analysis of Mutant In the application, CRISPR-Cas9 technology was used for site-directed mutagenesis in wheat genome. Specifically, in the application, sequence CTGGTGGACCAGCCCATGGT (SEQ ID NO: 21) was chosen as target sequence, which was a consensus sequence of TaMS7-A, TaMS7-B, and TaMS7-D gene, and at the $1017^{th}$-$1036^{th}$ nucleotide of TaMS7-A positive strand, at the $1035^{th}$ to $1054^{th}$, nucleotide of TaMS7-B positive strand, and at the $1038^{th}$ to $1057^{th}$ nucleotide of TaMS7-D positive strand. The sgRNA expression cassette with the target sequence and the Cas9 expression cassette were inserted into the same vector pAHC20, and introduced into wheat immature embryo with a plasmid which expressed bar gene through particle bombardment, then transgenic wheat plants were obtained.

Molecular identification of the transgenic wheat plants was performed, the mutations were identified at the target sites (SEQ ID NO. 31) of the TaMS7-A, TaMS7-B, and TaMS7-D genes: herein there were two types of mutation in the TaMS7-A gene, a 5 bp deletion (SEQ ID NO: 32) and a 55 bp insertion (SEQ ID NO: 33) respectively; there is one type of mutation in the TaMS7-B gene, a 13 bp deletion and a 54 bp insertion (SEQ ID NO: 34) simultaneously; and there were two types of the mutation in the TaMS7-D gene, one type is a 9 bp deletion (SEQ ID NO: 35), and the other type is a 7 bp deletion and a 103 bp insertion (SEQ ID NO: 36) simultaneously (refer to FIG. 3).

Observation of the plant which had homozygous mutation or biallelic mutation in the target sites of the TaMS7-A, TaMS7-B, and TaMS7-D genes revealed that the plants with this type of genotype showed thin, small and indehiscent anther without pollen grains and complete male sterile (refer to FIG. 4), and they were pollinated with the pollens of wild type to keep seeds; while the plant which had homozygous mutation or the biallelic mutation in only one or two genes of the TaMS7-A, TaMS7-B, and TaMS7-D genes didn't show a male sterile phenotype. It is indicated that the TaMS7 gene of the application is a recessive genic male sterile gene.

Embodiment 7. Transgenic Functional Complementation

Genomic DNA fragments (SEQ ID NO: 1. SEQ ID NO: 2 and SEQ ID NO: 3) of TaMS7-A, TaMS7-B, and TaMS7-D coding regions were constructed into pAHC20 vector respectively, 2.5 kb of native upstream promoter fragments (SEQ ID NO: 16, SEQ ID NO: 17 and SEQ ID NO: 18) were added in the front to drive the expression of the genes and 1.4 kb of downstream fragments (SEQ ID NO: 22: SEQ ID NO: 23 and SEQ ID NO: 24) were added at the back respectively, resulting in the vectors named as pAHC20pTaMS7-A:gTaMS7-A, pAHC20pTaMS7-B: gTaMS7-B and pAHC20pTaMS7-D:gTaMS7-D respectively.

The particle bombardment method was used to transform or co-transform the above three functional complementation vectors into wheat TaMS7-abd mutants, the pollen grains of transgenic positive plants were stained with $I_2$-KI and observed, showing that the pollen grains developed normally and were fertile. These analyses further prove that the TaMS7 genes participate in the regulation and control of pollen development, and the mutation of the TaMS7 genes results in a male sterile phenotype.

Embodiment 8. Application of TaMS7 Genes in New Generation Hybrid Breeding Technique TaMS7 genes could be applied in new generation of hybrid breeding technology, and the core idea of the technology was as follows: a wheat recessive genic male sterile mutant is used as the transformation acceptor material, and three closely-linked target genes were transformed into the sterile mutant. Thereinto, the fertility restoration gene can restore the fertility of the transformation acceptor, the pollen-inactivation gene can inactivate pollen grains containing the transgene, namely, the fertilization ability of those pollen grains is lost, the seed-marker gene can be used for sorting of the transgenic seeds from the non-transgenic seeds, and the sorted non-transgenic seeds can be used as the sterile line, while the transgenic seeds can be used as the maintainer line. The maintainer line can pollinate the sterile line to propagate the sterile line, meanwhile the maintainer line can self-pollinate to produce the offspring as the new generation of maintainer line. The technology utilizes biotechnology to produce a non-transgenic product, solves the problem of artificial or mechanical emasculation in wheat hybrid seed production, saves the steps of artificial or mechanical emasculation, can provide the seeds with higher quality and purity to planters, and saves labor cost.

Based on the above-mentioned principle, the inventors used the wheat TaMS7 gene to construct the plant expression vector. Before constructing the wheat expression vector, the inventors firstly transformed each of the three expression cassettes, ZmBT1-ZmAA TaMS7 and mChenyW, into the wheat respectively and further verified the function of each expression cassette. The results indicated that each expression cassette can work well as initially designed when they were transformed into the wheat independently.

Further, the inventor constructed a transformation vector by assembling the following DNA elements:

1) The pAHC20 vector was used as the backbone, into which the following expression cassettes were inserted operably;
2) The fertility restoring expression cassette of TaMS7 gene contains the fertility-related gene TaMS7, its promoter and terminator thereof which were all derived from a wheat variety CB037, three TaMS7genes from A. B and D genomes of wheat, namely TaMS7-A, TaMS7-B and TaMS7-D, may be simultaneously used for restoring the fertility of the wheat ms7 sterile line, or used for restoring the fertility of the wheat ms7 sterile line alone. Herein the genomic DNA sequence, the promoter sequence and the terminator sequence of TaMS7-Agene were shown in SEQ ID NO: 1, SEQ ID NO: 16 and SEQ ID NO: 22 respectively; the genomic DNA sequence, the promoter sequence and the terminator sequence of TaMS7-B gene were shown in SEQ ID NO: 2, SEQ ID NO: 17 and SEQ ID NO: 23 respectively, and the genomic DNA sequence, the promoter sequence and the terminator sequence of TaMS7-D gene were shown in SEQ ID NO: 3, SEQ ID NO: 18 and SEQ ID NO: 24 respectively.
3) The pollen inactivation gene expression cassette PG47: ZmBT1-ZmAA-1N2-1: the pollen inactivation gene was ZmAA, and the transit peptide was ZmBT1, the open reading frame of ZmBT1-ZmAA (nucleotide sequence thereof was shown in SEQ ID NO: 25) was ligated to the downstream of PG47 promoter (nucleotide sequence thereof was shown in SEQ ID NO: 26) and the upstream of IN2-1 terminator (nucleotide sequence thereof was shown in SEQ ID NO: 27).
4) The seed-marker gene expression cassette CaMV35S enhancer-LTP2: mCherryW-PINII: the open reading frame of mChenyW gene (SEQ ID NO: 28) was ligated between the CaMV35S enhancer-LTP2 promoter (SEQ ID NO: 29) and the PINII terminator (SEQ ID NO: 30), resulting in the gene expression cassette (CaMV35S enhancer-LTP2: mCherryW-PINII).

In the application, the inventors constructed a vector containing fertility restoration expression cassette with only a single TaMS7gene, the pollen inactivation gene expression cassette and seed-marker gene expression cassette. In addition, the vector containing the fertility restoration expression cassette with two TaMS7 genes, the pollen inactivation gene expression cassette and screening marker gene expression cassette was also constructed.

The particle bombardment method was used for transforming the above two vectors to wheat TaMS7-abd mutants, 12 and 9 transgenic positive plants in which the transgene is a single copy are obtained respectively. Pollen activity detection of the transgenic plants and the control plants was performed, the result showed that the proportion of the sterile pollen grains to total pollen grains in the non-transgenic wild type wheat plants was less than 2%, the anthers of the non-transgenic wheat TaMS7-abd mutant plants don't have pollen grains, while the anthers of the transgenic plant have pollen grains, and the proportion of the sterile pollen grains to the total pollen grains was about 50%. This results indicated that the TaMS7 gene in the vector provided in the application restored the male sterile phenotype of the TaMS7-abd mutant, in the meanwhile the ZmBT1-ZmAA gene was able to inactivate the pollen as expected.

Segregation analysis of fluorescence seeds and the non-fluorescence seeds was performed on the T1-generation seeds generated by the above transgenic plants, and showed a separation ratio of 1:1, namely fluorescence seeds carrying the exogenous gene and the non-fluorescence seeds without the exogenous gene showed a separation ratio of 1:1, indicating that each element of the vector provided by the application were well expressed as a whole, and the purpose of creating and breeding sterile line can be realized; herein, the TaMS7 gene can restore the fertility of the male sterile mutant acceptor, and the expression of the ZmBT1-ZmAA gene and the mChenyW gene was able to inactivate the pollen and marker the transgenic seeds by florescence as expected respectively. Therefore, a new generation of hybrid breeding technology system was established, namely on the basis of the wheat ms7 male genic sterile line, the above vector was transformed into it to form a maintainer line, the maintainer line containing the exogenous vector can be used for continuous production of the maintainer line and the ms7 sterile line, this technology system solved the problem that the wheat ms7 male genic sterile line cannot be propagated, and the obtained ms7 male sterile line can be used for production of the hybrid seeds.

The above technology system can also be acquired through the following methods, namely, the above vector was transformed into wild type common wheat, and the transgenic plant was crossed with the ms7 male sterile line, then the hybrid plant was selfing and the seeds were screened to acquire the maintainer line containing an exogenous vector in the background of the homozygous ms7 mutation, the maintainer line containing the exogenous vector can be used for continuous production of the maintainer line and the ms7 sterile line.

What is claimed is:

1. A method for propagating a male sterile line of wheat, wherein the method comprises the following steps:
   (a) producing a maintainer line by transforming an ms7 male sterile line with a vector that comprises: a fertility restoration gene TaMS7 which can restore the male fertility of the ms7 male sterile line; and a pollen inactivation gene, the expression of which disturbs the function or formation of a male gamete containing the pollen inactivation gene in a plant, so the fertile male gametes generated in the plant do not contain the vector, and a screening gene, which is used for sorting transgenic seeds and non-transgenic seeds; and
   (b) selfing the maintainer line plants transformed with the above vector to produce a ms7 male sterile line without the vector and a maintainer line seed containing the vector; or pollinating ms7 male sterile line plants with the pollen grains of the maintainer line plants to propagate the seeds of the ms7 male sterile line;
   a nucleotide sequence of the fertility restoring gene TaMS7 is selected from one of the following groups of sequences:
   (a) a nucleotide sequence as shown in SEQ ID NO: 1, 2, 3, 4, 5 or 6; or
   (b) a nucleotide sequence which codes an amino acid sequence as shown in SEQ ID NO: 7, 8 or 9.

2. The method of claim 1, wherein the fertility restoration gene TaMS7 is driven to express by a pollen-specific expression promoter.

3. The method of claim 1, wherein the pollen inactivation gene comprises, a barnase gene, an amylase gene, or a DAM methylase.

4. The method of claim 3, wherein the pollen inactivation gene is connected with a promoter specifically expressed in male gametes.

5. The method of claim 1, wherein the screening gene comprises, an antibiotics resistant gene, or a herbicide-resistant gene, or a fluorescent protein gene.

6. A producing or breeding method of a maintainer line of wheat, wherein the method comprises the following steps:
   (a) producing a maintainer line by transforming an ms7 male sterile line with a vector that comprises: a fertility restoration gene TaMS7 which can restore the male fertility of the ms7 male sterile line; and a pollen inactivation gene, the expression of which disturbs the function or formation of a male gamete containing the pollen inactivation gene in a plant, so the male gametes generated in the plant do not contain the vector, and a screening gene, which is used for sorting transgenic seeds and non-transgenic seeds,
   (b) selfing the maintainer line plants transformed with the above vector to produce a ms7 male sterile line without the vector and a maintainer line seed containing the vector, a nucleotide sequence of the fertility restoring gene TaMS7 is selected from one of the following groups of sequences:
   (a) a nucleotide sequence as shown in SEQ ID NO: 1, 2, 3, 4, 5 or 6; or
   (b) a nucleotide sequence which codes an amino acid sequence as shown in SEQ ID NO: 7, 8 or 9.

7. The producing or breeding method of claim 6, wherein the fertility restoration gene TaMS7 is driven by a pollen-specific promoter.

8. The producing or breeding method of claim 6, wherein the pollen inactivation gene comprises, a barnase gene, an amylase gene, or a DAM methylase.

9. The producing or breeding method of claim 8, wherein the pollen inactivation gene is connected with a promoter specifically expressed in male gametes.

10. The producing or breeding method of claim 6, wherein the screening gene comprises, an antibiotics resistant gene, or a herbicide-resistant gene, or a fluorescent protein gene.

11. The method of claim 2, wherein a nucleotide sequence of the pollen-specific expression promoter as shown in SEQ ID NO: 16, 17 or 18.

12. The method of claim 3, wherein the pollen inactivation gene is a maize α-amylase gene with a nucleotide sequence as shown in SEQ ID NO: 25.

13. The method of claim 4, wherein the promoter is a PG47 promoter or a Zm13 promoter.

14. The method of claim 5, wherein the screening gene comprises, a chloramphenicol-resistant gene, a hygromycin resistant gene, a streptomycin resistant gene, a miramycin resistant gene, a sulfonamide resistant gene, a glyphosate resistant gene, phosphinothricin resistant gene, a bar gene, a red fluorescence gene DsRED, a mCherry gene, a cyan fluorescence protein gene, a yellow fluorescence protein gene, a luciferase gene, or a green fluorescence protein gene.

15. The method of claim 7, wherein a nucleotide sequence of the pollen-specific promoter as shown in SEQ ID NO: 16, 17 or 18.

16. The method of claim 8, wherein the pollen inactivation gene is a maize α-amylase gene with a nucleotide sequence as shown in SEQ ID NO: 25.

17. The method of claim 10, wherein the screening gene comprises, a chloramphenicol-resistant gene, a hygromycin resistant gene, a streptomycin resistant gene, a miramycin resistant gene, a sulfonamide resistant gene, a glyphosate resistant gene, phosphinothricin resistant gene, a bar gene, a red fluorescence gene DsRED, a mCherry gene, a cyan fluorescence protein gene, a yellow fluorescence protein gene, a luciferase gene, or a green fluorescence protein gene.

* * * * *